United States Patent
Black

(10) Patent No.: US 11,065,080 B2
(45) Date of Patent: *Jul. 20, 2021

(54) METHOD AND APPARATUS TO ACCOUNT FOR TRANSPONDER TAGGED OBJECTS USED DURING CLINICAL PROCEDURES, EMPLOYING A TROCAR

(71) Applicant: Covidien LP, Mansfield, MA (US)

(72) Inventor: Patricia Black, Louisville, CO (US)

(73) Assignee: Covidien LP, Mansfield, MA (US)

( * ) Notice: Subject to any disclaimer, the term of this patent is extended or adjusted under 35 U.S.C. 154(b) by 273 days.

This patent is subject to a terminal disclaimer.

(21) Appl. No.: 16/316,693

(22) PCT Filed: Jul. 7, 2017

(86) PCT No.: PCT/US2017/041044
§ 371 (c)(1),
(2) Date: Jan. 10, 2019

(87) PCT Pub. No.: WO2018/013417
PCT Pub. Date: Jan. 18, 2018

(65) Prior Publication Data
US 2019/0151044 A1 May 23, 2019

Related U.S. Application Data

(60) Provisional application No. 62/378,515, filed on Aug. 23, 2016, provisional application No. 62/360,869, filed on Jul. 11, 2016.

(51) Int. Cl.
*A61B 90/98* (2016.01)
*A61B 17/34* (2006.01)
(Continued)

(52) U.S. Cl.
CPC .............. *A61B 90/98* (2016.02); *A61B 17/34* (2013.01); *A61B 17/3421* (2013.01);
(Continued)

(58) Field of Classification Search
CPC .......... A61B 90/98; A61B 17/34–3498; A61B 2017/00221; A61B 2090/0803–0806
See application file for complete search history.

(56) References Cited

U.S. PATENT DOCUMENTS 6,026,818 A 2/2000 Blair et al.
6,650,143 B1 11/2003 Peng
(Continued)

FOREIGN PATENT DOCUMENTS

JP 2014004237 A 1/2014
JP 2014068987 A 4/2014
(Continued)

OTHER PUBLICATIONS

International Search Report and Written Opinion of corresponding counterpart Int'l Appln. No. PCT/US2017/041044 dated Nov. 9, 2017.

(Continued)

*Primary Examiner* — Thaddeus B Cox
(74) *Attorney, Agent, or Firm* — Carter, DeLuca & Farrell LLP

(57) ABSTRACT

Medical procedure related objects (e.g., instruments, supplies) tagged with transponders (e.g., RFID transponders, dumb transponders) are accounted for in a medical or clinical environment via an accounting system using a number of antennas and interrogators/readers. A first set of antennas and RFID interrogator(s) interrogate portions of the environment for RFID tagged objects, for example proximate a start and an end of a procedure. A cannula of a trocar may include one or more trocar antennas positioned (Continued)

and oriented to integrate tapped objects that pass through a lumen of the cannula. Shielded packaging and/or shielded receptacles shield tagged objects, preventing interrogation except for those objects in unshielded portions of the environment. A data store may maintain information including a current status or count of each instrument or supply, for instance as checked in or checked out. A handheld antenna and/or second set of antennas interrogates a body of a patient for retained instruments or supplies tagged with dumb transponders.

20 Claims, 15 Drawing Sheets

(51) Int. Cl.
  *A61B 34/20* (2016.01)
  *A61B 90/53* (2016.01)
  *A61B 17/00* (2006.01)
  *A61B 17/29* (2006.01)
  *A61B 90/00* (2016.01)

(52) U.S. Cl.
  CPC .............. *A61B 34/20* (2016.02); *A61B 90/53* (2016.02); *A61B 17/29* (2013.01); *A61B 2017/00075* (2013.01); *A61B 2017/00221* (2013.01); *A61B 2034/2072* (2016.02); *A61B 2090/0805* (2016.02); *A61B 2090/0811* (2016.02)

(56) References Cited

U.S. PATENT DOCUMENTS

| | | | |
|---|---|---|---|
| 6,667,902 | B2 | 12/2003 | Peng |
| 6,671,040 | B2 | 12/2003 | Fong et al. |
| 6,700,151 | B2 | 3/2004 | Peng |
| 6,766,960 | B2 | 7/2004 | Peng |
| 6,777,757 | B2 | 8/2004 | Peng et al. |
| 6,791,891 | B1 | 9/2004 | Peng et al. |
| 6,798,693 | B2 | 9/2004 | Peng |
| 6,822,888 | B2 | 11/2004 | Peng |
| 6,856,540 | B2 | 2/2005 | Peng et al. |
| 6,898,116 | B2 | 5/2005 | Peng |
| 6,940,751 | B2 | 9/2005 | Peng et al. |
| 6,956,258 | B2 | 10/2005 | Peng |
| 6,972,986 | B2 | 12/2005 | Peng et al. |
| 6,992,925 | B2 | 1/2006 | Peng |
| 7,031,209 | B2 | 4/2006 | Wang et al. |
| 7,042,722 | B2 | 5/2006 | Suzuki et al. |
| 7,269,047 | B1 | 9/2007 | Fong |
| 7,471,541 | B2 | 12/2008 | Fong et al. |
| 7,609,538 | B1 | 10/2009 | Lee et al. |
| 7,696,877 | B2 | 4/2010 | Barnes et al. |
| 7,898,420 | B2 | 3/2011 | Blair et al. |
| 8,105,296 | B2 | 1/2012 | Morris et al. |
| 8,111,162 | B2 | 2/2012 | Barnes et al. |
| 8,181,860 | B2 | 5/2012 | Fleck et al. |
| 8,354,931 | B2 | 1/2013 | Blair |
| 8,358,212 | B2 | 1/2013 | Blair |
| 8,710,957 | B2 | 4/2014 | Blair et al. |
| 9,136,597 | B2 | 9/2015 | Blair |
| 9,514,341 | B2 | 12/2016 | Blair et al. |
| 9,592,962 | B1 | 3/2017 | Lee |
| 9,690,963 | B2 | 6/2017 | Buhler et al. |
| 9,717,565 | B2 | 8/2017 | Blair |
| 9,872,732 | B2 | 1/2018 | Blair |
| 10,193,209 | B2 | 1/2019 | Blair |
| 2004/0250819 | A1 | 12/2004 | Blair et al. |
| 2006/0241399 | A1 | 10/2006 | Fabian |
| 2007/0285249 | A1 | 12/2007 | Blair et al. |
| 2008/0294036 | A1 | 11/2008 | Hoi et al. |
| 2010/0108079 | A1 | 5/2010 | Blair |
| 2010/0109848 | A1 | 5/2010 | Blair et al. |
| 2011/0004276 | A1 | 1/2011 | Blair et al. |
| 2011/0181394 | A1 | 7/2011 | Blair |
| 2011/0237901 | A1* | 9/2011 | Duke ................. A61B 17/3462 600/208 |
| 2013/0016021 | A1 | 1/2013 | Blair |
| 2013/0088354 | A1* | 4/2013 | Thomas ................. A61B 90/90 340/572.1 |
| 2014/0262553 | A1* | 9/2014 | Pollock ................. G01G 17/04 177/1 |
| 2014/0303580 | A1 | 10/2014 | Blair |
| 2015/0054625 | A1 | 2/2015 | Blair et al. |
| 2015/0057653 | A1 | 2/2015 | Sugiyama |
| 2015/0119639 | A1 | 4/2015 | Ebata |
| 2015/0272688 | A1 | 10/2015 | Blair et al. |
| 2015/0363618 | A1 | 12/2015 | Fleck et al. |
| 2016/0089056 | A1 | 3/2016 | Limaye et al. |
| 2016/0210548 | A1 | 7/2016 | Blair |
| 2017/0086906 | A1 | 3/2017 | Tsuruta |
| 2017/0169172 | A1 | 6/2017 | Blair et al. |

FOREIGN PATENT DOCUMENTS

| | | |
|---|---|---|
| WO | 2014054398 A1 | 4/2014 |
| WO | 2015069496 A1 | 5/2015 |
| WO | 2015198618 A1 | 12/2015 |

OTHER PUBLICATIONS

U.S. Appl. No. 62/360,864, filed Jul. 11, 2016 and entitled "Method and Apparatus to Account for Transponder Tagged Objects Used During Clinical Procedures, Employing a Shielded Receptacle".
U.S. Appl. No. 62/360,866, filed Jul. 11, 2016 and entitled "Method and Apparatus to Account for Transponder Tagged Objects Used During Clinical Procedures Employing a Shielded Receptacle With Antenna".
U.S. Appl. No. 62/360,868, filed Jul. 11, 2016 and entitled "Method and Apparatus to Account for Transponder Tagged Objects Used During Clinical Procedures, For Example Including Count in and/or Count Out and Presence Detection".
U.S. Appl. No. 62/182,294, filed Jun. 19, 2015.
U.S. Appl. No. 62/164,412, filed May 20, 2015.
Extended European Search Report dated Feb. 18, 2020 corresponding to counterpart Patent Application EP 17828203.4.
Japanese Office Action issued in corresponding Japanese Application No. 2019-500642 dated Mar. 18, 2021, 13 pages.

\* cited by examiner

METHOD AND APPARATUS TO ACCOUNT FOR TRANSPONDER TAGGED OBJECTS USED DURING CLINICAL PROCEDURES, EMPLOYING A TROCAR

CROSS-REFERENCE TO RELATED APPLICATIONS

This application is a U.S. National Stage Application filed under 35 U.S.C. § 371(a) of International Patent Application Serial No. PCT/US2017/041044, filed Jul. 7, 2017, which claims the benefit of and priority to U.S. Provisional Patent Application Ser. No. 62/378,515, filed Aug. 23, 2016, and claims the benefit of and priority to U.S. Provisional Patent Application Ser. No. 62/360,869, filed Jul. 11, 2016, the entire disclosures of which are incorporated by reference herein.

BACKGROUND

Technical Field

The present disclosure generally relates to a wireless medical procedure environment, and, more particularly, accounting for transponder tagged medical or clinical procedure objects or items, for instance disposable gauze or sponges, and/or medical or clinical instruments typically employed in a medical or clinical environment in which medical or clinical procedures are performed.

Description of the Related Art

It is important to determine whether objects or items associated with a medical or clinical procedure are present or unintentionally retained in a patient's body before completion of a medical or clinical procedure. The medical or clinical procedure may, for example, take the form of a surgery or childbirth delivery. Such objects or items may take a variety of forms used in medical or clinical procedures. For example, the objects or items may take the form of instruments, for instance scalpels, scissors, forceps, hemostats, and/or clamps, which may be reusable after sterilization or alternatively may be single-use disposable objects or items. Also for example, the objects or items may take the form of related accessories and/or disposable objects, for instance disposable surgical sponges, gauzes, and/or absorbent pads. When used in surgery, failure to locate an object or item before closing the patient may require additional surgery, and in some instances may have serious adverse medical consequences. In other medical procedures, such as vaginal childbirth deliveries, failure to remove objects, for instance gauze or absorbent pads, can lead to infections and undesired complications.

Some hospitals have instituted procedures that include checklists or requiring multiple manual counts to be performed to track the use and return of objects or items during surgery. Such a manual approach is inefficient, requiring the time of highly trained personnel, and is prone to error.

Another approach employs wireless transponders that are attached to various objects or items used during surgery, and a wireless interrogation and detection system. Such an approach can employ "dumb" wireless transponders, i.e., wireless communications transponders that do not store and/or transmit any unique identifying information. Dumb wireless transponders have traditionally been employed for electronic article surveillance (EAS) to prevent loss of merchandise at retail locations. Alternatively, such an approach can employ radio frequency identification (RFID) wireless transponders, i.e., wireless communications transponders which do store and return a unique identifier in response to an interrogation signal emitted by an RFID interrogator or RFID reader.

In the approach that employs dumb wireless transponders, an interrogation and detection system includes a transmitter that emits pulsed wireless interrogation signals (e.g., radio or microwave frequency) and a detector for detecting wireless response signals returned by the dumb wireless transponders in response to the emitted interrogation signals. Such an automated system detects the presence or absence of dumb wireless transponders, but typically does not detect any unique identifying information. Since no power is required to operate the dumb wireless transponder, such an approach may have better range or better ability to detect objects or items retained within bodily tissue as compared to RFID wireless transponders communicating in similar ranges of wavelength and levels of power, but cannot uniquely identify the dumb wireless transponders. Examples of such an approach are discussed in U.S. Pat. No. 6,026,818, issued Feb. 22, 2000, and U.S. Patent Publication No. US2004/0250819, published Dec. 16, 2004.

In the approach that employs RFID wireless transponders, an interrogator or reader includes a transmitter that emits wireless interrogation signals (e.g., radio or microwave frequency) and a detector for detecting wireless response signals returned by the RFID wireless transponders in response to the emitted interrogation signals. Such an automated system advantageously detects the unique identifiers of the RFID wireless transponders; however since some of the power in the interrogation signal is required to operate the RFID wireless transponder such an approach may have shorter range or less ability to detect objects or items retained within bodily tissue as compared to dumb wireless transponders communicating in similar ranges of wavelength and levels of power. Examples of such an approach are discussed in U.S. Pat. Nos. 8,105,296; 8,181,860; and U.S. Patent Application Publication No. 2015/0363618.

Commercial implementation of such an automated system requires that the overall system be cost competitive, highly accurate, and easy to use. In particular, false negatives must be avoided to ensure that objects are not mistakenly left in the patient and false positives avoided to ensure valuable time and resources are not spent looking for objects which were not actually retained in the patient. Consequently, a new approach to prevention of foreign object retention in medical procedure environments is highly desirable.

BRIEF SUMMARY

An apparatus for use in clinical environments may be summarized as including a trocar, the trocar having a cannula with a proximal end and a second end, the cannula which delineates a lumen through the trocar that extends from the proximal end to the second end, with a proximal port at the proximal end which provides access to an interior of the lumen from an exterior of the trocar and with a distal port at the distal end which provides access to the interior of the lumen from the exterior of the trocar; and at least one trocar antenna, the at least one trocar antenna physically coupled to the trocar and positioned and oriented to provide wireless communications coverage of at least a portion of an interior of the lumen and any wireless communications identification transponders that pass through the lumen of the cannula or trocar.

The apparatus may further include an interrogator communicatively coupled to the at least one trocar antenna and operable to cause the at least one trocar antenna to emit at least one of radio or microwave frequency energy interrogation signals and to detect response signals from any exposed wireless communications identification transponders that pass through the lumen of the trocar. The at least one trocar antenna may be communicatively coupled to the interrogator via at least one electrical cable. The at least one trocar antenna may be communicatively detachably coupled to the interrogator via at least one electrical cable and a plug. The cannula of the trocar may shield the at least one trocar antenna from response signals emitted by any wireless communications identification transponders in the exterior of the trocar. The trocar antenna may include at least one electrically conductive coil that is concentric with at least one of the proximal or the distal ports or the lumen. The cannula of the trocar may include a metal. The trocar antenna may include an electrically insulative sheath that electrically insulates the trocar antenna from the cannula. The cannula of the trocar may include a plastic. The trocar antenna may be encased in the plastic of the cannula. The at least one trocar antenna may be positioned and oriented to provide coverage of an entirety of the interior of the lumen of the trocar and all wireless communications identification transponders in the interior of the lumen of the trocar. The at least one trocar antenna may be positioned and oriented to provide coverage of the proximal port and all wireless communications identification transponders passing through the proximal port. The at least one trocar antenna may be positioned and oriented to provide coverage of the distal port and all wireless communications identification transponders passing through the distal port. The at least one trocar antenna may include a first trocar antenna positioned and oriented to provide coverage of the proximal port and all wireless communications identification transponders passing through the proximal port, and at least a second trocar antenna positioned and oriented to provide coverage of the distal port and all wireless communications identification transponders passing through the distal port. The interrogator may include at least one radio frequency identification (RFID) interrogator communicatively coupled to the at least one trocar antenna and operable to cause the at least one trocar antenna to emit at least one of radio or microwave frequency energy interrogation signals and to detect response signals from any wireless communications identification transponders in the interior of the lumen without detecting any wireless communications identification transponders that outside the interior of the lumen.

The at least one RFID interrogator may include at least one processor, the at least one processor communicatively coupled to the at least one interrogator; and at least one nontransitory processor-readable medium that stores at least one of processor-executable instructions or data, execution of which causes the at least one processor to store an itemization of each of the wireless communications identification transponders that pass through at least a portion of the interior of the lumen.

The at least one RFID interrogator may include at least one processor, the at least one processor communicatively coupled to the at least one interrogator; and at least one nontransitory processor-readable medium that stores at least one of processor-executable instructions or data, execution of which causes the at least one processor to itemize each of the wireless communications identification transponders that enters the lumen of the trocar via the proximal port; and itemize each of the wireless communications identification transponders that exits the lumen of the trocar via the proximal port.

Execution of the at least one of processor-executable instructions or data may further cause the at least one processor to compare the itemization of each of the wireless communications identification transponders that exits the lumen of the trocar via the proximal port with the itemization of each of the wireless communications identification transponders that enters the lumen of the trocar via the proximal port.

The at least one RFID interrogator may include at least one processor, the at least one processor communicatively coupled to the at least one interrogator; and at least one nontransitory processor-readable medium that stores at least one of processor-executable instructions or data, execution of which causes the at least one processor to itemize each of the wireless communications identification transponders that exits the lumen of the trocar via the distal port; and itemize each of the wireless communications identification transponders that enters the lumen of the trocar via the distal port.

Execution of the at least one of processor-executable instructions or data may further cause the at least one processor to compare the itemization of each of the wireless communications identification transponders that enters the lumen of the trocar via the distal port with the itemization of each of the wireless communications identification transponders that exits the lumen of the trocar via the distal port.

The trocar may further include a seal located at least proximate the proximal end and an obturator located proximate the distal end. The proximal port may be sized and dimensioned to receive pieces of disposable gauze, each piece of disposable gauze tagged with a respective radio frequency identification (RFID) wireless communications identification transponder.

A method of operation of an apparatus, the apparatus which may include a trocar having a cannula with a lumen having a proximal port at a proximal end of the lumen and a distal port at a distal end of the lumen, at least one trocar antenna, and at least one interrogator communicatively coupled to the at least one trocar antenna, may be summarized as including causing, by the interrogator, the at least one trocar antenna to emit at least one interrogation signal having a range that covers at least a portion of an interior of the lumen of the cannula; detecting, by the interrogator, any response signals to the at least one interrogation signal, the response signals returned from any wireless communications identification transponders in the portion of the interior of the lumen of the cannula; identifying, by the interrogator, each of a number of wireless communications identification transponders in the portion of the interior of the lumen of the cannula based on the detected response signals; and storing to at least one nontransitory processor-readable medium information that identifies each of the wireless communications identification transponders or items physically associated respective wireless communications identification transponders that pass through at least a portion of the interior of the lumen. Storing information that may identify each of the wireless communications identification transponders or items physically associated respective wireless communications identification transponders that pass through at least a portion of the interior of the lumen may include storing an itemization of each of wireless communications identification transponders that pass through at least a portion of the interior of the lumen comprises:

Storing an itemization of each of wireless communications identification transponders that pass through at least a portion of the interior of the lumen may include itemizing each of the wireless communications identification transponders that enters the lumen of the trocar via the proximal port; and itemizing each of the wireless communications identification transponders that exits the lumen of the trocar via the proximal port.

The method may further include comparing the itemization of each of the wireless communications identification transponders that exits the lumen of the trocar via the proximal port with the itemization of each of the wireless communications identification transponders that enters the lumen of the trocar via the proximal port.

The method may further include causing a notification to be provide in response to a discrepancy in the comparison of the itemization of each of the wireless communications identification transponders that exits the lumen of the trocar via the proximal port with the itemization of each of the wireless communications identification transponders that enters the lumen of the trocar via the proximal port.

Storing an itemization of each of the wireless identification transponders that pass through at least a portion of the interior of the lumen may include itemizing each of the wireless communications identification transponders that exits the lumen of the trocar via the distal port; and itemizing each of the wireless communications identification transponders that enters the lumen of the trocar via the distal port.

The method may further include comparing the itemization of each of the wireless communications identification transponders that enters the lumen of the trocar via the distal port with the itemization of each of the wireless communications identification transponders that exits the lumen of the trocar via the distal port.

The method may further include causing a notification to be provide in response to a discrepancy in the comparison of the itemization of each of the wireless communications identification transponders that enters the lumen of the trocar via the distal port with the itemization of each of the wireless communications identification transponders that exits the lumen of the trocar via the distal port.

The method may further include generating a time and date stamp that represents a time and date of the itemization; and storing the generated time and date stamp logically associated with the itemization.

The method may further include causing an alert to be provided in response to existence of a discrepancy between the identities of the wireless transponders identified entering and exiting the cannula.

The method may further include determining, by at least one processor, a first count of a total number of items that enter the lumen of the cannula based on the detected response signals; and determining, by the at least one processor, a second count of a total number of items that exit the lumen of the cannula based on the detected response signals.

The method may further include determining, by at least one processor, a first count of a total number of items that enter the lumen of the cannula via the proximal port based on the detected response signals; and determining, by the at least one processor, a second count of a total number of items that exit the lumen of the cannula via the proximal port based on the detected response signals.

The method may further include determining, by at least one processor, a first count of a total number of items that enter the lumen of the cannula via the distal port based on the detected response signals; and determining, by the at least one processor, a second count of a total number of items that exit the lumen of the cannula via the distal port based on the detected response signals.

An article for use in clinical environments may be summarized as including a cannula with a proximal end and a distal end, the cannula which delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; and at least a first trocar antenna, the first trocar antenna physically coupled to the cannula and positioned and oriented to provide wireless communications coverage of at least a portion of an interior of the lumen and any wireless communications identification transponders that pass through the lumen of the cannula.

The article may further include at least one electrical cable electrically coupled to the at least the first trocar antenna.

The article may further include a plug physically coupled to an end of the at least one electrical cable and detachably coupleable to an interrogator. The cannula may be flexible and formed of a plastic. The cannula may be transparent. The cannula may include a metal.

The article may further include an electrically insulative sheath that electrically insulates the first trocar antenna from the cannula.

The article may further include at least a second trocar antenna, the second trocar antenna physically coupled to the cannula and positioned and oriented to provide wireless communications coverage of at least a portion of the interior of the lumen and any wireless communications identification transponders that pass through the lumen of the cannula.

The lumen of the cannula may be sized to moveably receive an obturator of a trocar. The cannula may be coupled to a head of a trocar, for example detachably coupleable to a head of a trocar.

An apparatus for use in clinical environments may be summarized as including: a tubular instrument, the tubular instrument having a cannula with a proximal end and a distal end, the cannula which delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; at least one antenna, the at least one antenna physically coupled to the tubular instrument and positioned and oriented to provide wireless communications coverage of at least a portion of an interior of the lumen and any wireless communications transponders that pass through the lumen of the cannula; and an interrogator communicatively coupled to the at least one antenna and operable to cause the at least one trocar antenna to emit at least one of radio or microwave frequency energy interrogation signals, to detect response signals from any exposed wireless communications transponders that pass through the lumen of the cannula, and to determine a direction of passage of any exposed wireless communications transponders that pass at least partially along the lumen. The interrogator may include at least one processor that determines the direction of passage of any exposed wireless communications transponders that pass at least partially along the lumen based on a detection of a number of successive passages events past respective ones of two or more antennas. The interrogator may include at least one processor that determines the direction of passage of any exposed wireless communications transponders that pass at least partially along the lumen based on a frequency of the response signal.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
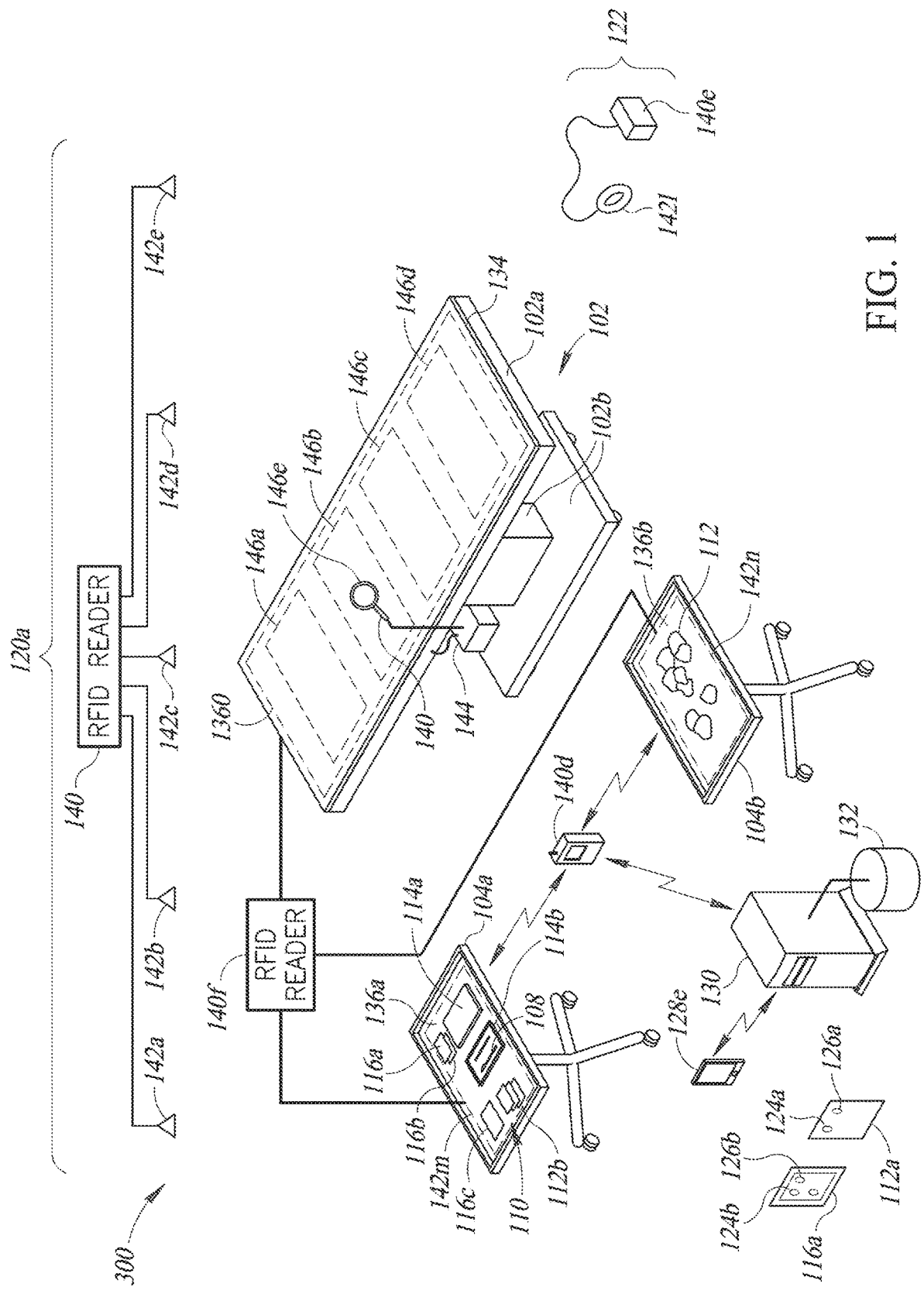
FIG. 1 is an isometric view of a medical or clinical environment in which a medical or clinical procedure is performed, according to one illustrated implementation, and which includes a patient support structure, a number of tables or stands on which medical or clinical procedure instruments and supplies are carried, a number of antennas and one or more radio frequency identification interrogators, a number of antennas and a dumb transponder interrogator, an accounting system communicatively coupled to the interrogators, a number of pieces of medical or clinical procedure objects or items and associated packaging which may advantageously shield the medical or clinical procedure objects or items until opened.

FIG. 1 shows a medical or clinical environment 300 in which a medical or clinical procedures are performed, according to one illustrated implementation.

The medical or clinical procedure environment 300 may take any of a variety of forms, for example a surgical environment or operating room in which surgeries are performed, or an emergency room (ER) in which various medical or clinical procedures are performed. Other medical or clinical procedure environments 300 may take the form of a patient room, examination room or physician's office, etc., in which medical or clinical procedures are performed, or a dedicated labor and delivery (L&D) room in which vaginal child birth or deliveries are performed.

The medical or clinical procedure environment 300 typically includes a patient support structure 102 that can carry a patient (not shown) or portion thereof. The medical procedure environment 300 typically includes a number of accessory tables or stands 104 (only one shown in FIG. 1), for example to hold medical or clinical procedure instruments 108 (one shown) and/or supplies 110. The medical or clinical procedure environment 300 may optionally include one or more receptacles (not shown), for example to collect used medical or clinical procedure instruments 108 and/or supplies 110. The receptacle(s) may advantageously shield (e.g., Faraday cage) the contents of the receptacle(s) from wireless communications (e.g., radio frequencies, microwave frequencies) at least while the receptacle(s) is in a closed configuration.

The medical or clinical procedure environment 300 will typically include one or more medical or clinical procedure related objects or items, for example one or more implements or instruments 108 (only one shown) and one or more supplies 110. As a non-limiting example, instruments 108 may take the form of scalpels, scissors, forceps, hemostats, clamps, retractors, and/or trocars. As a non-limiting example, supplies 110 may take the form of disposable or reusable supplies, and for instance, sponges (e.g., surgical sponges), gauze and/or padding 112a, 112b (only two called out in FIG. 1, collectively 112).

The medical or clinical procedure environment 300 may include one or more totes or trays 114a, 114b (two shown, collectively 114) that carry instruments 108 and/or supplies 110. The totes or trays 114 may be hermetically sealed (e.g., tote or tray 114a) until opened (e.g., tote or tray 114b) for use, in order to maintain the contents of the totes or trays 114 sterile prior to introduction of the contents into the medical or clinical procedure environment 300 for use. As discussed in detail below, the totes or trays 114 may advantageously shield (e.g., Faraday cage) the contents of the totes or trays 114 from wireless communications (e.g., radio frequencies, microwave frequencies) at least until the totes or trays 114 are opened and/or the contents removed from the totes or trays 114.

The medical or clinical procedure environment 300 may include one or more pieces of packaging 116a, 116b, 116c (e.g., packets, envelopes or sleeves, three shown, collectively 116) which carry instruments 108 and/or supplies 110. The packaging 116 may be hermetically sealed (e.g., packets or envelopes 116a, 116b) until opened (e.g., packet or envelope 116c) for use, to maintain the contents of the packaging sterile prior to introduction into the medical or clinical procedure environment 300 for use. The packaging 116 may, for example, take the form of hermetically sealed packets or envelopes 116a, 116b that enclose a number of sponges (e.g., surgical sponges), gauze and/or padding 112. As discussed in detail below, the packaging 116 may advantageously shield (e.g., Faraday cage) the contents of the packaging 116 from wireless communications (e.g., radio frequencies, microwave frequencies) at least until the packaging 116 is opened and/or the contents removed from the packaging 116.

The medical or clinical procedure related instruments or implements 108 and/or supplies 110, totes or trays 114 and/or packaging 116 are typically held, supported or carried by the tables or stands 104 when not in use.

As illustrated and described elsewhere herein, one or more implements or instruments 108 and/or one or more supplies 110 may have one or more wireless communications transponders physically attached thereto. As illustrated and described elsewhere herein, for example one or more trays or totes 114 and/or one or more pieces of packaging 116 may have one or more wireless communications transponders physically attached thereto.

The medical or clinical procedure environment 300 will typically include one or more pieces of medical or clinical procedure related equipment (not shown), for instance one or more lamps, anesthetizing equipment, heart/lung machines or cardiopulmonary bypass machines, ventilators, cauterization equipment, defibrillator, aspirator equipment, infusion pump, dialysis machine, intra-aortic balloon pump, various monitors such as blood pressure, heart or pulse rate, pulse-oxygen (pulse-ox or pulse oximetry) sensor, temperature, EKG sensors or electrodes or electrical conductivity sensors, intracranial pressure sensors, pH sensors, other dedicated medical diagnostic, therapeutic or monitoring equipment, etc. One or more of these pieces of medical or clinical procedure related equipment may be a source of electronic noise, making it difficult to identify wireless communications transponders in the medical or clinical procedure environment 300.

Where the medical procedure environment 300 is an operating room or operating theater, there will typically be a number of medical providers present. For instance, medical providers present during a surgery may include a surgeon, a first assistant surgeon, a second assistant surgeon, an anesthetist, an instrument nurse, a supply nurse, and/or one or more circulating nurses (not illustrated). The surgeons or physicians are typically responsible for working directly on a patient, for example cutting, excising, cauterizing, suturing, ablating, fastening, implanting, etc. The anesthetist is typically responsible for administering anesthesia and monitoring certain vital signs, such as blood pressure, pulse, oxygen level and/or blood gases. The instrument and supply nurses, respectively, may be responsible for handing instruments 108 and supplies 110 from the instrument and supply tables 104 to the surgeons, and collecting the instruments 108 and supplies 110 after use. Some or all of the instruments and/or supplies may be deposited in the receptacle 106a after use.

The medical procedure environment 300 may include one or more wireless communications identification interrogation systems, for example one or more radio frequency identification (RFID) interrogation systems 120a. The RFID interrogation system(s) 120a is(are) operable to interrogate wireless communications identification transponders, for example RFID transponders or RFID tags 124a, 124b (only two shown in FIG. 1, collectively 124), receive return signals from RFID transponders or RFID tags 124 which encode unique identifiers, and thereby uniquely identify the RFID transponders or RFID tags 124 within the range of the RFID interrogation system(s) 120a. The RFID transponders or RFID tags 124 store and return unique identifiers (e.g., unique at least within a large enough set to supply a large clinical facility for a month). The RFID transponders or RFID tags 124 may, preferably, take the form of passive RFID transponders or RFID tags which omit batteries and derive power for operation from the interrogation signal. While denominated as "radio frequency," commercial RFID interrogator systems 120a and RFID transponders or tags 124 typically operate or communicate in the low or high frequency (e.g., radio frequency) and/or ultra-high frequency (e.g., microwave frequency) portions of the electromagnetic spectrum. Hence, consistent with common usage in the field of automatic data collection, use of the terms radio frequency and/or RFID is not limited to interrogation systems and wireless communications transponders that employ radio frequency communications, but also include interrogation systems and wireless communications transponders that employ microwave frequency communications.

The medical procedure environment 300 may include one or more wireless communications presence/absence interrogation systems 122. The presence/absence interrogation system(s) 122 is operable to interrogate wireless communications dumb transponders 126a, 126b (only two shown in FIG. 1, collectively 126), receive return wireless communications dumb transponders 126 which do not encode unique identifiers, and determine at least one of a presence or absence of the wireless communications dumb transponders 126 in the range of the wireless communications presence/absence interrogation system(s) 122. The wireless communications dumb transponders 126 are typically simple LC resonant circuits, and do not store, encode or return unique identifiers. The wireless communications presence/absence interrogation system(s) 122 and the wireless communications dumb transponders 126 typically communicate a lower frequency range than RFID interrogator system(s) 120a and the RFID transponders or RFID tags 124. This may advantageously result in better range than obtainable by the RFID interrogator system(s) 120a, and increased ability to detect a wireless communications dumb transponder 126 retained in bodily tissue, even where a patient is obese. In some instances, the frequency range of the RFID interrogator system(s) 120a and the wireless communications presence/absence interrogation system(s) 122 does not overlap.

The medical procedure environment 300 may include one or more computers or terminals 128 to allow entry and/or access to information, for example an inventory of instruments 108 and supplies 110 for a particular medical or clinical procedure. The computers or terminals 128 can take a large variety of forms, for example a desktop computer or terminal, laptop computer, netbook computer, tablet computer, or smartphone. The computers or terminals 128 may include a computer housing 128a which houses one or more processors, one or more memories (e.g., RAM, ROM, FLASH), one or more hard disk drives, one or more solid state drives, etc. The computers or terminals 128 may include a display 128b, and one or more user input devices, for example a touch screen or keyboard 128c and/or pointer device such as a computer mouse 128d. For instance, the medical or clinical procedure environment 200 includes a tablet computer 128e to enter and/or provide access to information, for example an inventor of instruments 108 and/or supplies 110 for a given medical or clinical procedure.

The medical procedure environment 300 may include an accounting system 130 that is operable to maintain in a nontransitory computer- or processor-readable medium 132 an inventory of instruments 108 and supplies 110 at least for a particular medical or clinical procedure. The RFID interrogation system(s) 120a and presence/absence interrogation system(s) 122 are each communicatively coupled to the accounting system 130 via one or more wired or wireless communications channels (e.g., tethered, serial networked). The accounting system 130 can receive information autonomously generated by the RFID interrogation system(s) 120a and presence/absence interrogation system(s) 122, allowing automated itemization and inventorying functions to be performed. The computers or terminals 128 may be communicatively coupled to the accounting system 130 via one or more wired or wireless communications channels (e.g., tethered, serial networked) allowing manual entry of information, for instance manual counts of instruments 108 and/or supplies 110, as well as checking of the status of defined items or of the inventory for a given medical or clinical procedure.

The accounting system 130 may be communicatively coupled to a backend accounting or validation or inventory system (not shown), which stores information in at least one nontransitory computer- or processor-readable medium. The backend accounting or validation or inventory system may be located on the premises of the medical or clinical procedure environment 300, or located remotely therefrom. The backend accounting or validation or inventory system may be communicatively coupled to the accounting system 130 via any variety of wired or wireless communications channels including one or more networks. The backend accounting or validation or inventory system may, for example, manage inventory for multiple medical or clinical procedure environments 300. The accounting system 130 and/or the backend accounting or validation or inventory system may, for example, produce tamper-proof time and date stamps, logically associated with inventory as evidence of counts of instruments 108 and supplies 110, for instance at the start and at the end of a medical or clinical procedure.

The patient support structure 102 may take the form of a table (e.g., operating table), bed or other structure that may include a patient support surface 102a and a pedestal or base 102b that supports the patient support surface 102a. The patient support surface 102a should have dimensions sufficient to support at least a portion of a patient (not shown) during a medical or clinical procedure, for instance during surgery. Hence, the patient support surface 102a may have a length of six feet or more and a width of two feet or more. The patient support surface 102a may have two or more articulated sections (not shown), or may be an unarticulated or unitary structure as illustrated. Hinges or other coupling structures may couple any articulated sections. For instance, hinges may be located along a longitudinal axis of the patient support surface 102a at locations that would approximate the anticipated position of between a patient's legs and torso and between the patient's torso and head.

The patient support surface 102a is preferably made of a rigid material and is preferably radiolucent, allowing radiological imaging (e.g., X-rays, CAT scans, MRIs). Various radiolucent materials may be employed, for instance carbon fiber or radiolucent plastics (e.g., resin impregnated carbon fiber). Such advantageously allows radiological technologies to be employed, for example X-ray imaging. For example, the patient support surface 102a may be molded from plastics such as an acrylic or a phenolic resin (e.g., commercially available under the trademark SPAULDITE®). In some embodiments, the patient support structure 102 may include a frame. The frame may be made of a metal which may not be radiolucent. In such embodiments, the frame preferably makes up a small percentage of the total area of the patient support surface 102a. The patient support surface 102a may be capable of withstanding multiple cycles of sterilization (e.g., chemical, heat, radiation, etc.). A large variety of surgical tables, patient beds and other structures capable of supporting or carrying a patient or a portion of a patient are commercially available. Many of these commercially available structures include electric motors and electronics. Typically, there is no or minimal regulation of non-ionizing electromagnetic radiation generated by such electric motors and electronics. Hence, many medical or clinical procedure environments 300 in which medical or clinical procedures are performed tend to be electromagnetically noisy environments.

The patient support structure 102 may include one or more film receiving receptacles (not shown). The film receiving receptacles may be spaced relatively below a patient support surface 102a of the patient support structure 102. The film receiving receptacles are sized, dimensioned and/or positioned to receive film, for example X-ray film. The film receiving receptacles may be sized and/or dimensioned to receive a film tray or other film holder (not illustrated) which holds the film. Along with the use of radiolucent materials, such advantageously allows a patient X-ray images or other radiological images of the patient to be produced, generated or made, while the patient is supported by the patient support structure 102. As used herein an in the claims, the term radiolucent means substantially transmissive to energy in the X-ray portion of the electromagnetic spectrum, that is passing sufficient X-ray energy to produce an X-ray image at standard power levels and standard conditions employed in conventional medical imaging.

The pedestal or base 102b may be fixed, or may be moveable. The pedestal or base may include one or more actuators (e.g., motors, pumps, hydraulics, etc.) and/or drive mechanisms (e.g., gears, mechanical couplings) or linkages (not shown) that allow a position and/or orientation of the patient support surface 102a to be adjusted. For example, the pedestal or base may telescope to allow the patient support surface 102a to be mechanically raised and lowered. Also for example, the pedestal or base may allow the patient support surface 102a to be mechanically tilted or rotated about an axis that is perpendicular to the patient support structure 102.

The patient support structure 102 may include one or more drapes, mattresses or pads 134, and/or may include one or more sheets (not illustrated). The drapes, mattresses or pads 134 may take a variety of forms, and may be disposable, or may be capable of withstanding multiple cycles of sterilization (e.g., chemical, heat, radiation, etc.). The drapes, mattresses or pads 134 are preferably radiolucent (e.g., interior of cotton or a foam material such as a closed or an open cell foam rubber or LATEX®, liquid or a gas, exterior of cotton, nylon, rayon or other natural or synthetic materials). The drapes, mattresses or pads 134 may take a conventional form, for example cotton, open cell or a closed cell foam rubber, with or without an appropriate cover. Alternatively, the drapes, mattresses or pads 134 may include one or more bladders (e.g., dual layer urethane envelope) to receive a fluid (e.g., air, water, etc.) to selectively inflate one or more portions of the mattresses or pads, and/or to control a temperature of one or more portions of the mattresses or pads. In such embodiments, the fluid should be radiolucent. The drapes, mattresses or pads 134 may be detachably secured to the patient support structure 102 via various fasteners, for instance ties, or hook and loop fastener commonly available under the trademark VELCRO®.

The tables or stands 104 may take a variety of forms. For instance, the tables or stands 104 may include one or more instrument tables, supply tables, Mayo stands or tables and/or back tables. The table(s) or stand(s) 104 may include a generally planar surface, which may be supported by legs, or supported by brackets attached to a fixed structure such as a wall. Some tables or stands 104 may include a recess or opening (not shown), for example to receive a bucket or tray. The table(s) or stand(s) 104 are typically made of a metal, for instance a stainless steel. One or more of the table(s) or stand(s) 104 may be movable, for example including wheels or coasters. One or more of the table(s) or stand(s) 104 may be fixed. A portion of one or more tables or stands 104 may extend over the patient support structure 102, and hence the patient, during use. Often the table or stand 104 will be covered by one or more sterile drapes or mats 136a. In addition to carrying instruments 108 and/or supplies 110, the tables or stands 104 may carry any other object including medical procedure related equipment, trays or totes 114, buckets, implants, etc.

Optionally one or more receptacle(s) (not shown) are preferably wirelessly shielded (e.g., Faraday cages), to prevent wireless (e.g., radio or microwave frequency) communications between an interior of the receptacle and an exterior thereof, at least in a closed configuration. The one or more receptacle(s) may receive medical instruments 108 or supplies 110, for example used sponges or gauze, and hence may be denominated as waste receptacles. In some implementations, the receptacle(s) 106a may receive unused instruments 108 or supplies 110, for example to allow interrogation in a shielded environment that is shielded from the various sources of noise present in many medical or clinical environments. The receptacle(s) may take a variety of forms, for example buckets. Such receptacle(s) may be open, or may have a cover, lid or door that is selectively positionable between open (illustrated in FIG. 1) and closed positions or configurations. Such receptacle(s) may have a variety of shapes and sizes, and may be made of any number of materials, including but not limited to metals and plastics. The receptacle(s) may include a disposable liner. The receptacle(s) may, for example, include wheels or coasters to allow easy movement thereof, or may omit such.

Figure 8A:
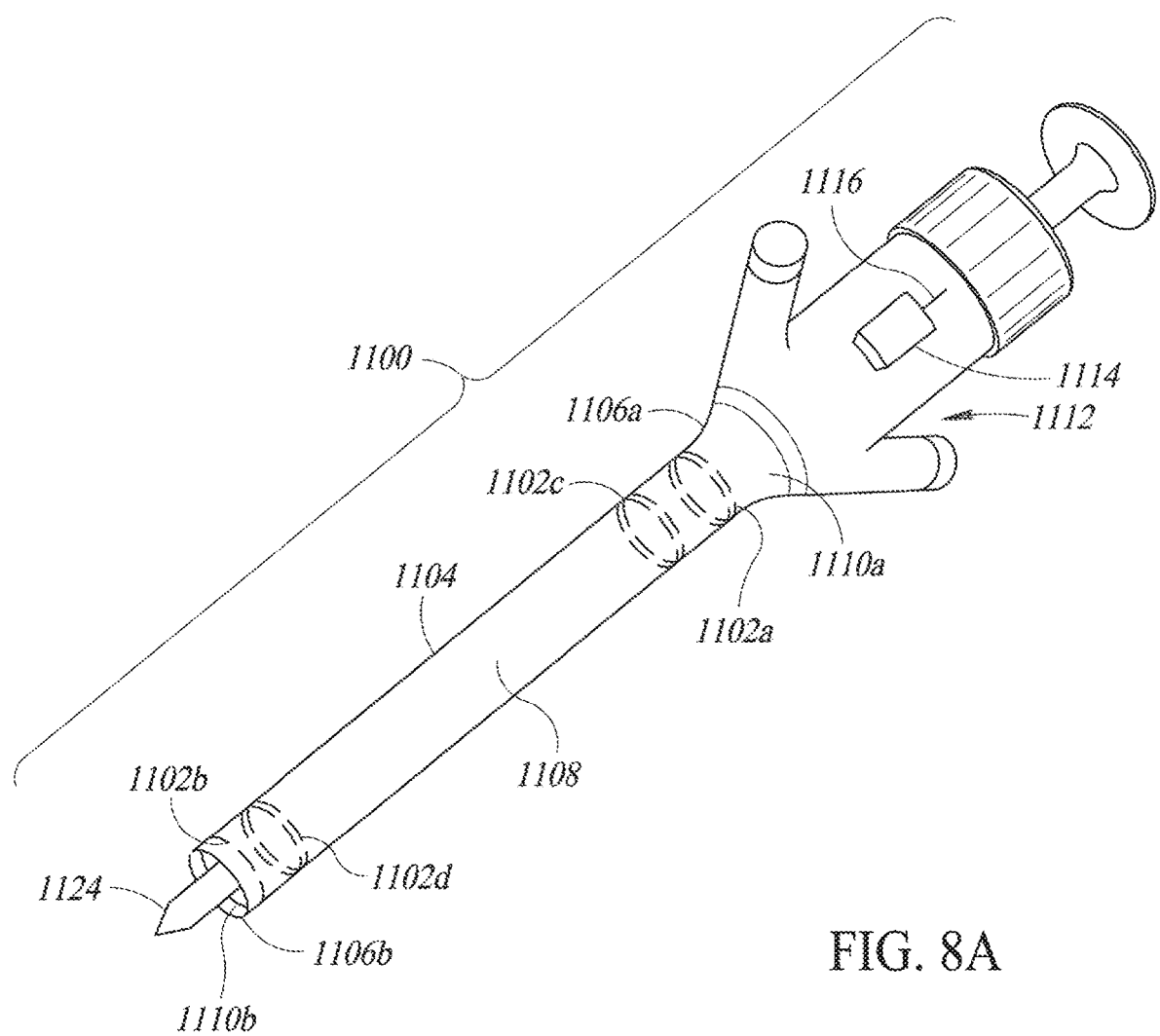
FIG. 8A is an isometric view of a trocar with a number of antennas and an interrogator or reader communicatively coupled to the antennas, according to at least one illustrated implementation.
Figure 8B:
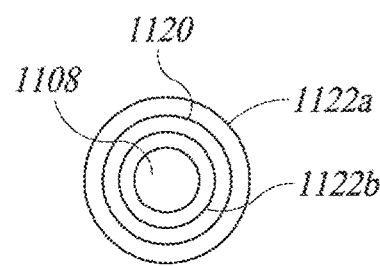
FIG. 8B is a cross-sectional view of a trocar with a number of antennas, according to at least one illustrated implementation.
Figure 8C:
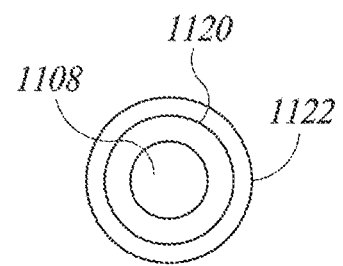
FIG. 8C is a cross-sectional view of a trocar with a number of antennas, according to at least one another illustrated implementation.

The RFID interrogation system(s) may, for example, include one or more the trocar RFID interrogation system(s) (FIGS. 8A-8C, which each include one or more antennas 1102a, 1102b (FIGS. 8A-8C, two shown, singularly or collectively 1102) communicatively coupled to an RFID interrogator or reader 1114 (FIGS. 8A-8C) to interrogate supplies 110 and/or instruments 108 that pass through a lumen 1108 (FIGS. 8A-8C) of a trocar 1100 (FIGS. 8A-8C), for instance as discussed elsewhere herein.

Alternatively or additionally, the RFID interrogation system(s) may, for example, include one or more room-based RFID interrogation system 120a that includes one or more RFID interrogators or readers 140 and one or more antennas 142a-142e (collectively 142) communicatively coupled to the RFID interrogator(s) or reader(s) 140. Commonly available RFID interrogators or readers 140 typically operate in high frequency range (e.g., 13.56 Hz), or ultra-high frequency range (e.g., 433 MHz, 860 MHz to 960 MHz). Other implementations can include a greater or lesser number of RFID interrogators or readers 140 and/or antennas 142. Antennas 142 may be spaced about the medical or clinical environment 300, providing complete or substantially complete (e.g., 85% or greater) coverage of unshielded portions of the medical or clinical environment 300.

Alternatively or additionally, the RFID interrogation system(s) may, for example, include one or more hand-held RFID interrogator 140d to interrogate instruments and/or supplies 110 on the first table or stand 104a, and/or on the second table or stand 104b, and/or optionally on the patient support surface 102a for instance as discussed elsewhere herein.

Alternatively or additionally, the RFID interrogation system(s) may, for example, include one or more body-worn hand-held RFID interrogation system 120c including a body-worn interrogator or reader 140e and a body-worn antenna 142l, to interrogate instruments and/or supplies 110 on the first table or stand 104a, and/or on the second table or stand 104b, and/or optionally on the patient support surface 102a, for instance as discussed elsewhere herein.

Alternatively or additionally, the RFID interrogation system(s) may, for example, include one or more drapes or mats 136a, which each include one or more antennas 142m, communicatively coupled to an RFID interrogator or reader 140f to interrogate instruments and/or supplies 110 on the first table or stand 104a, and/or on the second table or stand 104b, and/or optionally on the patient support surface 102a, for instance as discussed elsewhere herein.

The presence/absence interrogation system(s) 122 includes one or more presence/absence interrogators or readers 144 and one or more antennas 146a-146e communicatively coupled to the presence/absence interrogator(s) or reader(s) 144. The presence/absence interrogators or readers 144 may operate in the frequency range extending, for example, from about 137 kHz to about 160 kHz. Some of the antennas 146a-146d may be located in the drape, mattress or pad 134 used on the patient support surface 102a, providing complete or substantially complete coverage of a patient's body or sterile volume. One or more antennas 146e may be hand-held, for example incorporated as part of a wand 148. The handheld antenna 146e is communicatively coupled to the presence/absence interrogator(s) or reader(s) 144 by a wired or wireless communications path, for example via a coaxial cable or other communication path. The drape, mattress or pad 134 used on the patient support surface 102a may employ the structures and methods disclosed in U.S. Pat. No. 9,136,597. The presence/absence interrogation system(s) 122 may, for example, employ the structures and algorithms disclosed in U.S. Patent Application Publication No. 2011/0004276 and U.S. Patent Application Publication No. 2015/0272688.

The antennas 146 may take a variety of forms, for example coil antennas, dipole antennas, and/or slot antennas. Portions of one or more of the antennas 146 may overlap. For example, where the antennas 146 are coil antennas, each formed of one or more coils, a portion of an area enclosed by an outermost coil of each antenna may overlap a portion of an area enclosed by an outermost coil of a neighboring antenna. In such embodiments, neighboring antennas 146 may be electrically insulated from one another, for example by one or more electrically insulative layers or substrates. For example, successively adjacent antennas 146 may be carried on opposite surfaces (e.g., opposed outer surfaces, or multiple inner surfaces, or one or more outer and inner surfaces) of a single substrate. As discussed in more detail below, the antennas 146 may advantageously be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) may be radiolucent. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

In one implementation, personnel (e.g. counting nurse) can employ a hand-held RFID interrogator 140d to interrogate instruments and/or supplies 110 on the first table or stand 104a, on the second table or stand 104b, and/or optionally on the patient support surface 102a. The handheld RFID interrogator 140d may be set to a "count in" or "scan in" mode or configuration, in which the hand-held RFID interrogator 140d identifies each unique identifier that is read as identifying an item being added to an inventory. The personnel (e.g. counting nurse) can employ the same hand-held RFID interrogator 140d to interrogate instruments and/or supplies 110 on the second table or stand 104b. For example, the personnel (e.g. counting nurse) can employ the hand-held RFID interrogator 140d to subsequently interrogate instruments and/or supplies 110 (e.g., used or discarded surgical sponges, gauze and/or padding 112c) on the second table or stand 104b. The hand-held RFID interrogator 140d may be set to a "count out" or "scan out" mode or configuration, in which the RFID interrogator 140d identifies each unique identifier that is read as identifying an item being removed from an inventory or otherwise being accounted for or having an accounted for status in the inventory. The hand-held RFID interrogator 140d may be set to a "count out" or "scan out" mode or configuration, in which the RFID interrogator 140d identifies each unique identifier that is read as identifying an item being removed or accounted for in the inventory. The hand-held RFID interrogator 140d may supply the information (e.g., unique identifier and count in or count out status) to the accounting system 130, for example via one or more wired or wireless communications channels.

In another implementation, personnel (e.g. counting nurse) can employ a body-worn hand-held RFID interrogation system 120c to interrogate instruments and/or supplies 110 on the first table or stand 104a, on the second table or stand 104b, and/or optionally on the patient support surface 102a.

Figure 7:
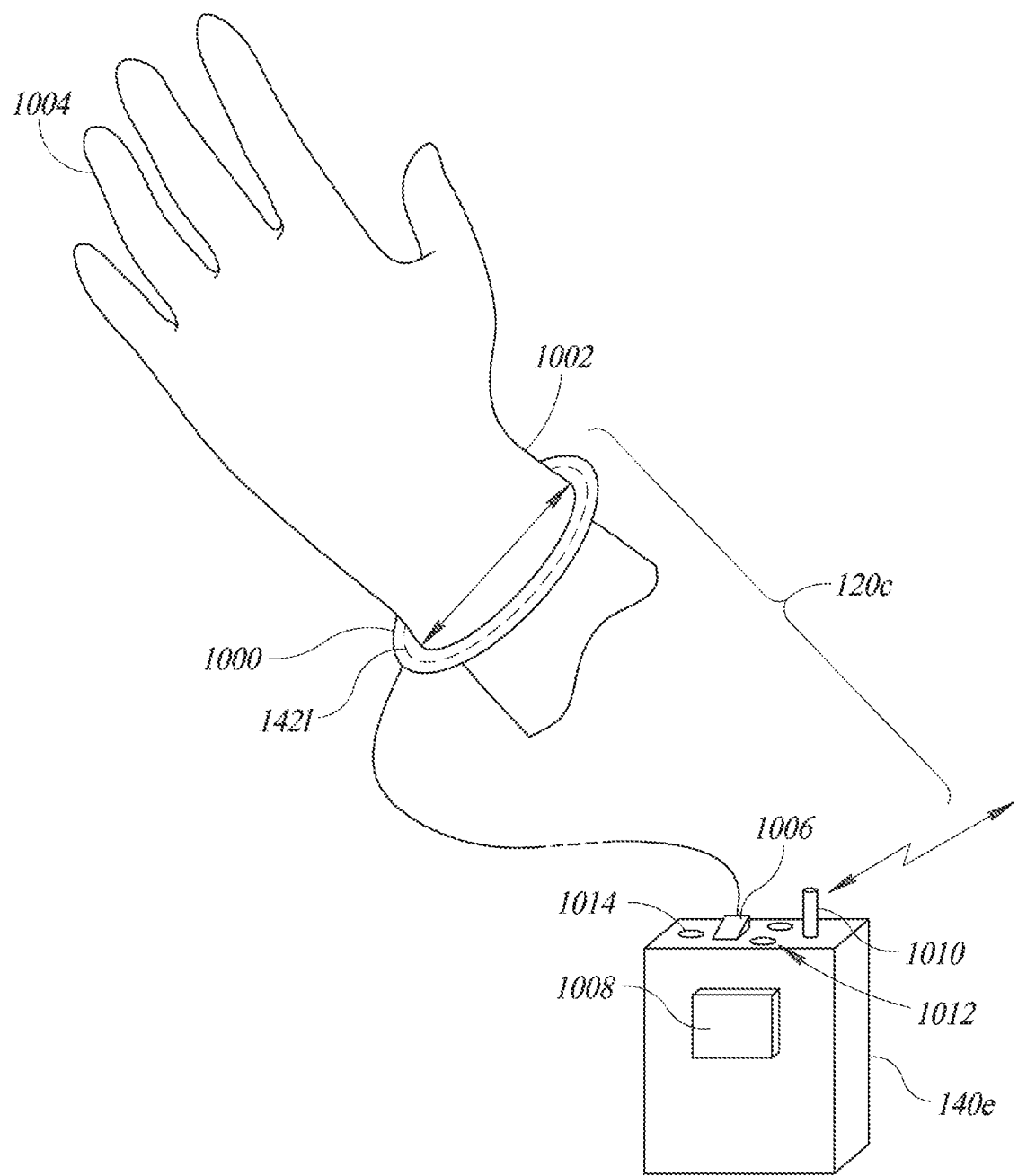
FIG. 7 is an isometric view of a body-worn antenna and interrogator or reader communicatively coupled to the antenna, according to at least one illustrated implementation.

As illustrated in FIG. 1 and better illustrated in FIG. 7, the body-worn hand-held RFID interrogation system 120c may include a body-worn antenna 142l, for example encased in a bracelet 1000 (FIG. 7) worn on a wrist 1002 or as encased in a ring worn on a finger 1004, and a body-worn interrogator or reader 140e. The body-worn interrogator or reader 140e may include a receptacle 1006 to detachably communicatively couple the body-worn antenna 142l to the body-worn interrogator or reader 140e. The body-worn interrogator or reader 140e may, for example have a clip 1008 to allow the body-worn interrogator or reader 140e to be worn on a belt or vest. The body-worn interrogator or reader 140e may include an antenna 1010 to provide communications with the accounting system 130 (FIG. 1). The body-worn interrogator or reader 140e may include one or more visual indicators (e.g., LEDs, LCDs) 1012 and/or speakers 1014 for producing visual and aural alerts.

Returning to FIG. 1, the body-worn interrogator or reader 140e may be set to a "count in" or "scan in" mode or configuration, in which the body-worn interrogator or reader 140e identifies each unique identifier that is read as identifying an item being added to an inventory as the personnel sweeps the antenna over the first table 104a. The personnel (e.g., counting nurse) can employ the same hand-held body-worn interrogator or reader 140e to interrogate instruments and/or supplies 110 on the second table or stand 104b. For example, the personnel (e.g., counting nurse) can employ the body-worn interrogator or reader 140e to subsequently interrogate instruments and/or supplies 110 (e.g., used or discarded surgical sponges, gauze and/or padding 112c) on the second table or stand 104b. The body-worn interrogator or reader 140e may be set to a "count out" or "scan out" mode or configuration, in which the body-worn interrogator or reader 140e identifies each unique identifier that is read as the personnel sweeps the antenna over the first table 104a as identifying an item being removed from an inventory or otherwise being accounted for or having an accounted for status in the inventory. The body-worn interrogator or reader 140e may be set to a "count out" or "scan out" mode or configuration, in which the body-worn interrogator or reader 140e identifies each unique identifier that is read as identifying an item being removed or accounted for in the inventory. The body-worn interrogator or reader 140e may supply the information (e.g., unique identifier and count in or count out status) to the accounting system 130, for example via one or more wired or wireless communications channels.

In a further implementation, each of the first and the second tables or stands 104a, 104b may carry a respective drape or mat 136a, 136b, which each include one or more antennas 142m, 142n communicatively coupled to an RFID interrogator or reader 140f. A first set of drape- or mat-based antennas 142m can interrogate instruments and/or supplies 110 on the first table or stand 104a. The RFID interrogator 140f may identify each unique identifier that is read via the first set of drape- or mat-based antennas 142 as identifying an item being added to an inventory. A second set of drape- or mat-based antennas 142n can interrogate instruments and/or supplies 110 on the second table or stand 104b. The RFID interrogator 140f may identify each unique identifier that is read via the second set of drape- or mat-based antennas 142n as identifying an item being removed from or accounted for in the inventory. The RFID interrogator 140f may supply the information (e.g., unique identifier and count in or count out status) to the accounting system 130, for example via one or more wired or wireless communications channels.

While illustrated using two drapes or mats 136a, 136b and associated sets of antennas 142m, 142n, some implementations can use a single drape or mat 126a, for example moving the first drape or mat 136a from the first table or stand 104a to the second table or stand 104b. While illustrated using two drapes or mats 136a, 136b and associated sets of antennas 142m, 142n, some implementations can use a single drape or mat 136a, for example using the first table or stand 104a to initially count or scan in, and subsequently using the first table or stand 104a to count or scan out the instruments 108 and/or supplies 110. In such implementations, the interrogator or reader 140f may be manually switched between a "count in" or "scan in" mode or configuration and a "count out" or "scan out" mode or configuration. The RFID interrogator 140f may supply the information (e.g., unique identifier and count in or count out status) to the accounting system 130, for example via one or more wired or wireless communications channels.

In a yet a further implementation, the patient support surface 102a of the patient support structure 102 may carry one or more drapes or mats 134, which each include one or more antennas 142o communicatively coupled to an RFID interrogator or reader 140f. A set(s) of drape- or mat-based antennas 142o can interrogate instruments and/or supplies 110 on the patient support surface 102a of the patient support structure 102. In such an implementation, the interrogator or reader 140f may be manually switched between a "count in" or "scan in" mode or configuration and a "count out" or "scan out" mode or configuration. The RFID interrogator 140f may supply the information (e.g., unique identifier and count in or count out status) to the accounting system 130, for example via one or more wired or wireless communications channels.

In an even yet a further implementation, the medical procedure environment 300 may include one or more wireless communications identification interrogation systems, for example one or more radio frequency identification (RFID) interrogation systems 120a with associated antennas 142a-142e. Antennas 142 may be spaced about the medical or clinical environment 300, providing complete or substantially complete (e.g., 85% or greater) coverage of unshielded portions of the medical or clinical environment 300, and hence denominated as room antennas.

Figure 2A:
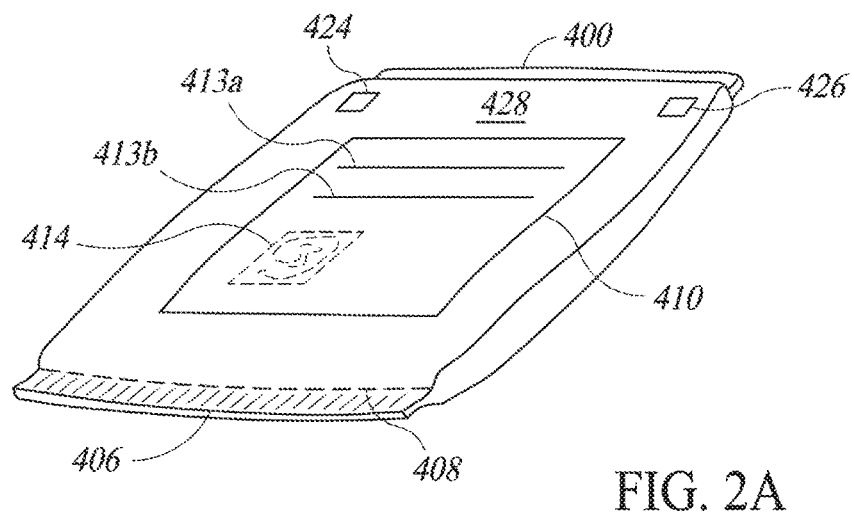
FIG. 2A is an isometric view of a piece of shielded packaging in the form of a shielded envelope or shielded pouch shown in an unopened configuration, the piece of shielded packaging which contains or holds one or more medical or clinical objects or items, each of which includes one or more wireless communications transponders, according to at least one illustrated implementation, the shielded packaging which prevents the wireless communications transponders from receiving interrogations signals and/or responding to interrogations signals at least until the shielded packaging is opened.
Figure 2B:
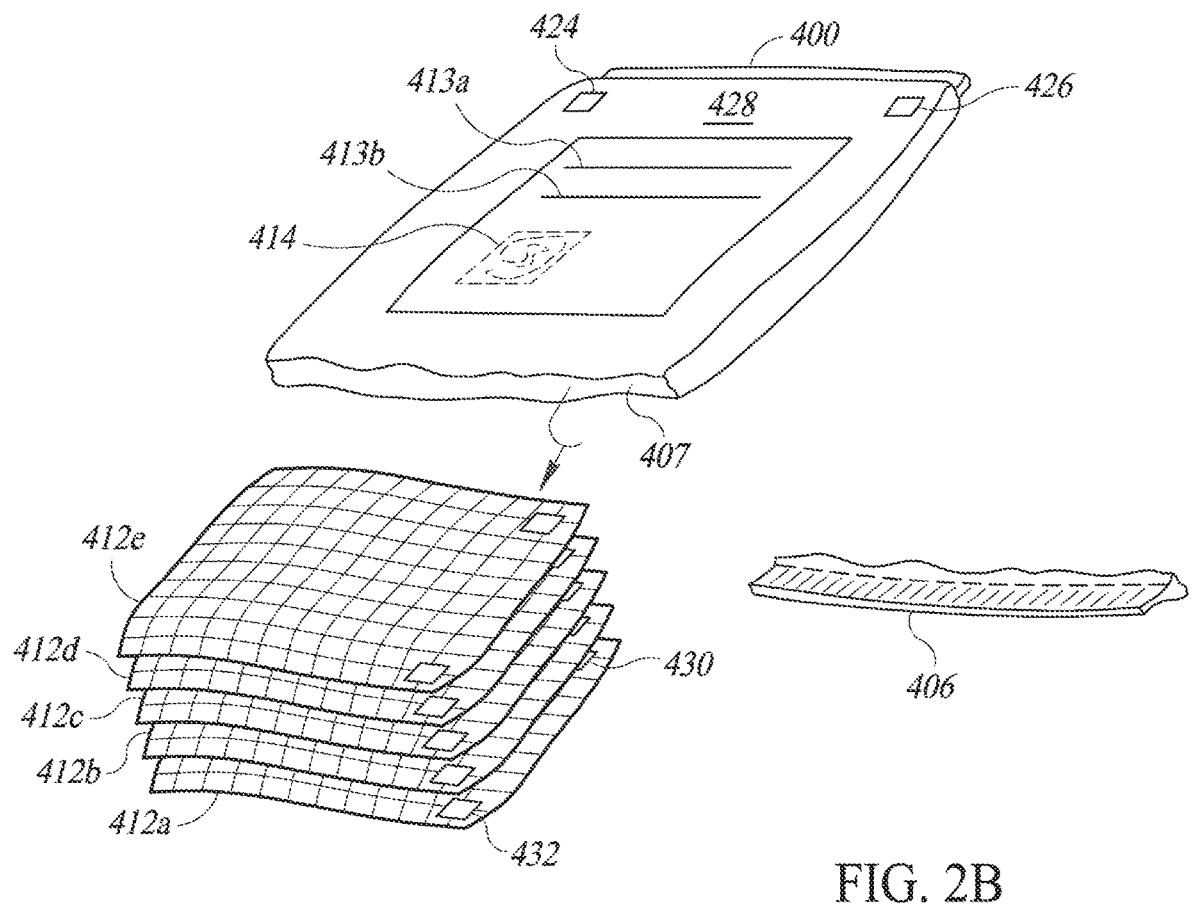
FIG. 2B is an isometric view of the shielded envelope of FIG. 2A shown in an opened configuration, along with a number of medical or clinical objects or items which have been removed from the piece of shielded packaging, and which each includes one or more wireless communications RFID transponders and/or one or more wireless communications dumb transponders, according to at least one illustrated implementation.
Figure 2C:
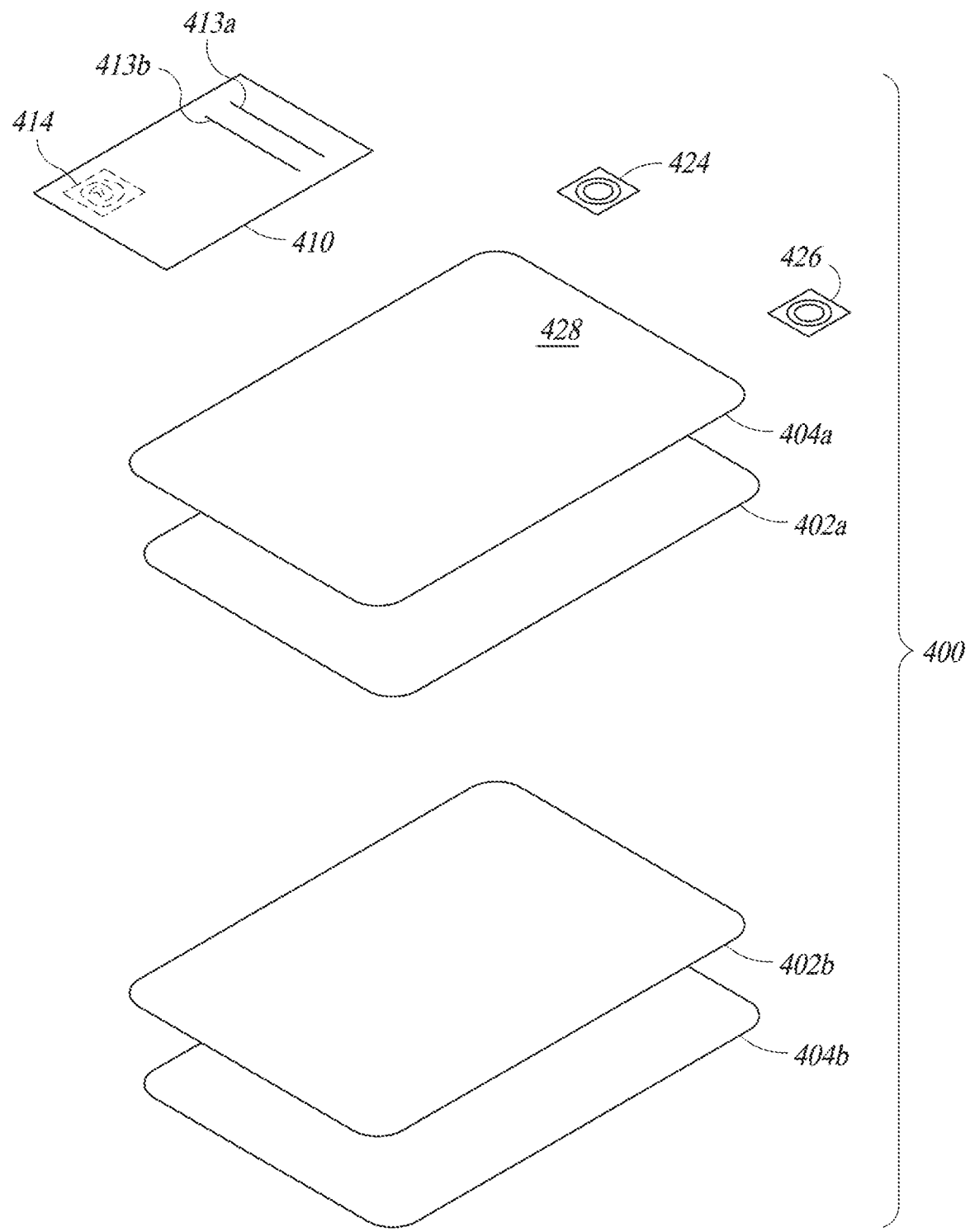
FIG. 2C is an exploded isometric view of the shielded envelope or shielded pouch of FIGS. 2A and 2B, which, according to at least one illustrated implementation, can include a packaging layer, a foil shield layer, and which itself may carry or bear a label with identifying information, and/or one or more wireless communications RFID transponders and/or one or more wireless communications dumb transponders.
Figure 2D:
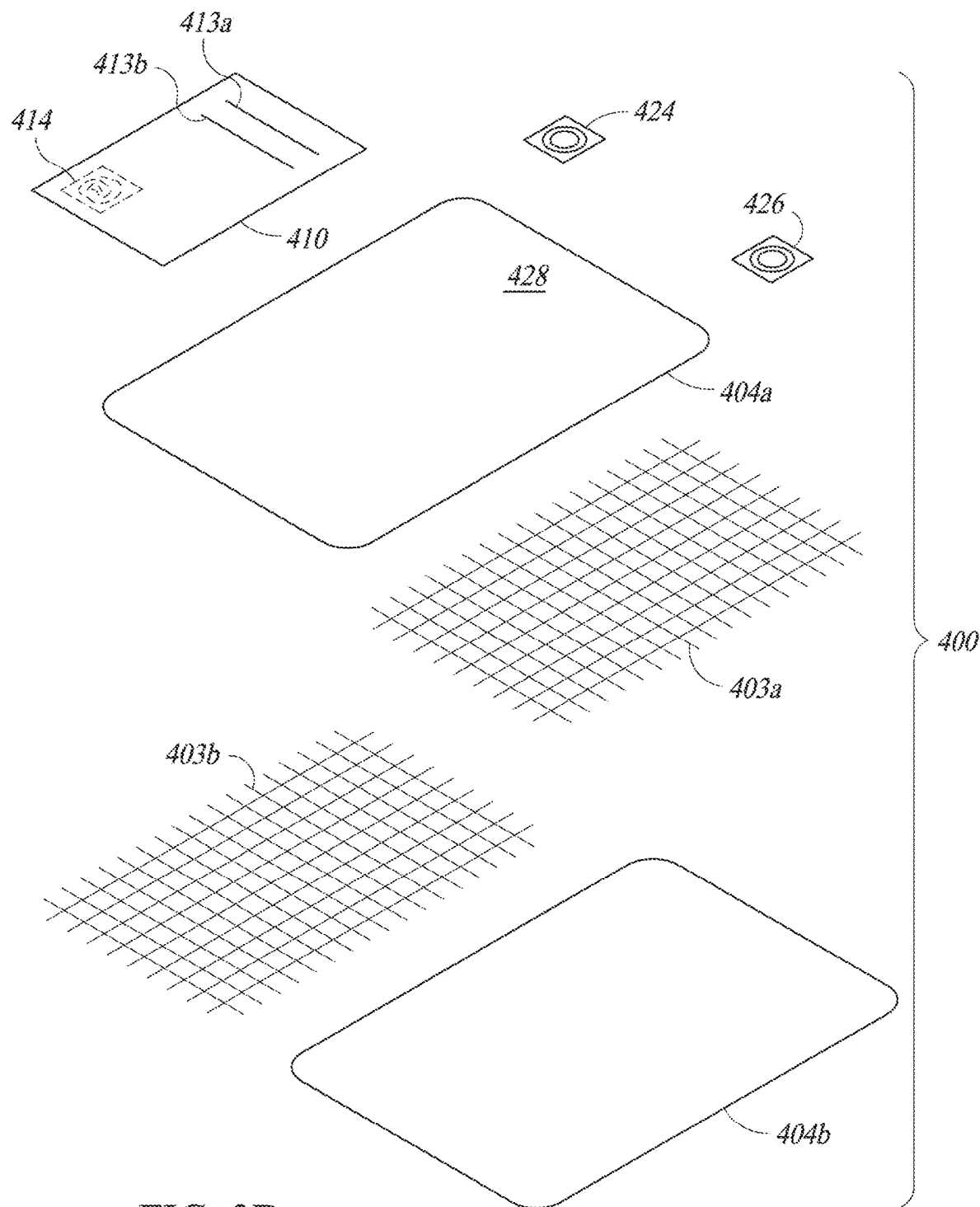
FIG. 2D is an exploded isometric view of the shielded envelope or shielded pouch of FIGS. 2A and 2B, which, according to at least one illustrated implementation, can include a packaging layer, an electrically conductive mesh or grid shield layer, and which itself may carry or bear a label with identifying information, and/or one or more wireless communications RFID transponders and/or one or more wireless communications dumb transponders.

FIG. 2A shows a piece of shielded packaging 400 in a sealed or closed configuration, according to at least one illustrated implementation. FIG. 2B shows the piece of shielded packaging 400 in an unsealed or opened configuration, with the contents of the shielded packaging 400, in the form of surgical sponges, gauze and/or padding 412a-412e (collectively 412, five shown in FIG. 2B), removed from the piece of shielded packaging 400. FIG. 2C shows an exploded view of one implementation of the piece of shielded packaging 400. FIG. 2D shows an exploded view of another implementation of the piece of shielded packaging 400.

The piece of shielded packaging 400 can, as illustrated, take the form of, for example, a packet, envelope or sleeve. The piece of shielded packaging 400 can, for example, take the form of an electrically conductive foil packet, envelope or sleeve that serves as a shield (e.g., Faraday cage) to communications (e.g., radio frequencies, microwave frequencies) for the contents of the shielded packaging 400. The piece of shielded packaging 400 can, for example, comprise aluminum foil, copper foil, or a metalized substrate, for instance a metalized Mylar®, heat-sealable metalized paper polyethylene, heat-sealable metalized plastic laminate, etc. For example, as illustrated in FIG. 2C, the piece of shielded packaging 400 can include a pair of electrically conductive foil layers 402a, 402b laminated to respective non-electrically conductive outer packaging layers 404a, 404b. Alternatively, the shielded packaging 400 may comprise an electrically conductive mesh or grid, which may be laminated to, or sandwiched between electrically non-conductive materials 404a, 404b (e.g., Mylar®, plastic laminate, paper polyethylene, paper). For example, as illustrated in FIG. 2D, the piece of shielded packaging 400 can include a pair of electrically conductive mesh or grid layers 403a, 403b laminated to respective non-electrically conductive outer packaging layers 404a, 404b.

The piece of shielded packaging 400 can, for example, be closed via an adhesive or heat sealed 406 along at least one edge. The contents can advantageously be loaded into and sealed in an interior 407 (FIG. 2B) of the piece of shielded packaging 400 in a sterile environment. The piece of shielded packaging 400 may include a slit, notch or tear line 408, that facilitates opening, for example by tearing.

The piece of shielded packaging 400 may bear labeling 410. The label 410 can, for example, include one or more human-readable pieces of information 413a, 413b (e.g., alpha-numeric text or legends). The label 410 can, for example, include one or more optically machine-readable pieces of information, for example one or more machine-readable symbols 414 (e.g., one-dimensional or barcode symbols, two-dimensional or matrix code symbols). The information in the human-readable pieces of information 413a, 413b and/or encoded in the machine-readable symbol(s) 414 can identify the contents of the piece of shielded packaging 400 by name, quantity, manufacturer, and lot and/or batch number.

The piece of shielded packaging 400 may bear one or more wireless communications transponders, for example an RFID transponder 424 and/or a dumb wireless transponder 426. The RFID transponder and/or dumb wireless transponders 424, 426 are preferably located on an exterior 428 of the piece of shielded packaging 400 or at least exterior to a shield layer of the piece of shielded packaging 400. The RFID transponder and/or dumb wireless transponders 424, 426 can be retained via an adhesive or can be heat welded or RF welded to the piece of shielded packaging 400. The RFID transponders 424 can store and return information that identifies the contents of the piece of shielded packaging 400 by name or description (e.g., 4×4 gauze), quantity (e.g., 10 pieces), manufacturer, lot and/or batch number, date of manufacture and/or expiration date.

The contents, for example absorbent surgical sponges, gauze and/or padding 412, may bear one or more wireless communications transponders, for example an RFID transponder 430 (only one called out in FIG. 2B) and/or a dumb wireless transponder 432 (only one called out in FIG. 2B). The RFID transponder and/or dumb wireless transponders 430, 432 can be attached to an exterior surface or an inner surface (e.g., interior folded surface) of the surgical sponges, gauze and/or padding 412. The RFID transponder and/or dumb wireless transponders 430, 432 can be retained via an adhesive, can be heat welded or RF welded to the surgical sponges, gauze and/or padding 412, stitched thereto by cotton or other natural or synthetic thread or fiber, and/or clamped thereto via one or more fasteners (clamp, rivet, snap, staple). The structures and techniques disclosed in U.S. Patent Application Publication No. 2014/0303580, U.S. patent application Ser. No. 15/003,524, and U.S. patent application Ser. No. 15/053,956 may be employed to secure the RFID transponder and/or dumb wireless transponders 424 to the surgical sponges, gauze and/or padding 412. The RFID transponders 430 can store and return information that identifies the contents of the piece of shielded packaging 400 by name, quantity, manufacturer, lot and/or batch number, date of manufacture and/or expiration date.

Figure 3A:
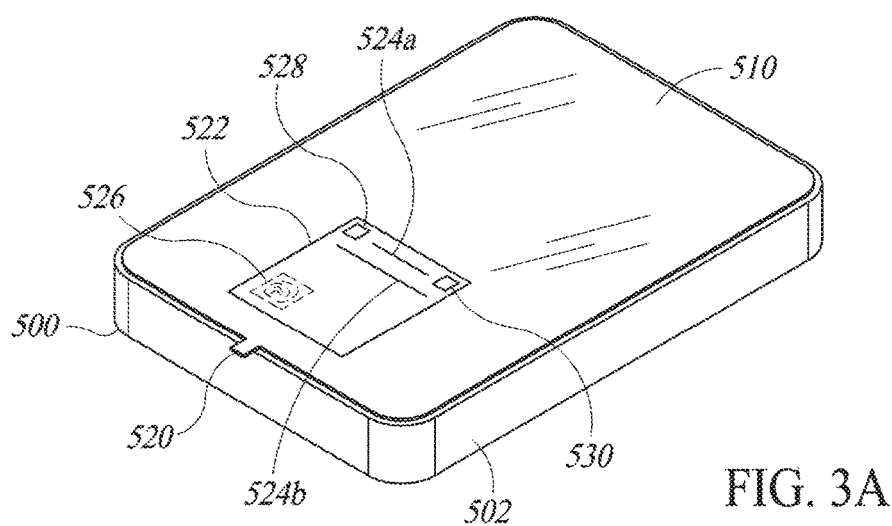
FIG. 3A is an isometric view of the piece of shielded packaging in the form of a shielded tote or tray shown in an unopened configuration, the piece of shielded packaging which contains or holds one or more medical or clinical objects or items, each of which includes one or more wireless communications transponders, according to at least one illustrated implementation, the shielded packaging which prevents the wireless communications transponders from receiving interrogations signals and/or responding to interrogations signals at least until the shielded packaging is opened.
Figure 3B:
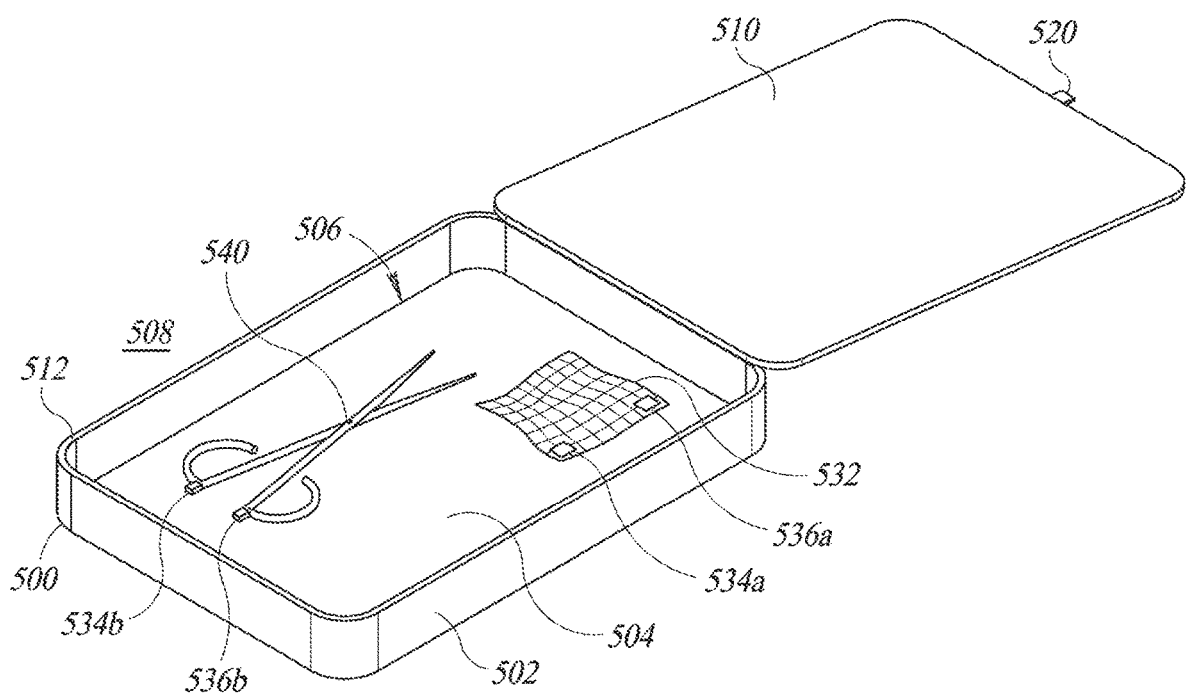
FIG. 3B is an isometric view of the shielded tote or tray of FIG. 3A shown in an opened configuration along with a number of medical or clinical objects or items which have been removed from the piece of shielded packaging, and which each includes one or more wireless communications RFID transponders and/or one or more wireless communications dumb transponders, according to at least one illustrated implementation.
Figure 4A:
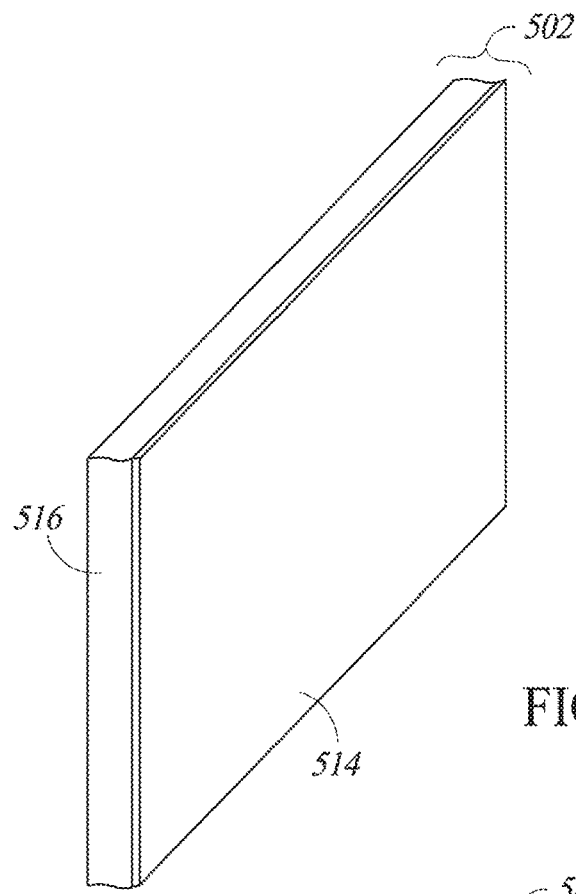
FIG. 4A is an isometric view of a portion of the shielded tote or shielded tray of FIGS. 3A and 3B, which, according to at least one illustrated implementation, can include a packaging layer and a foil shield layer.
Figure 4B:
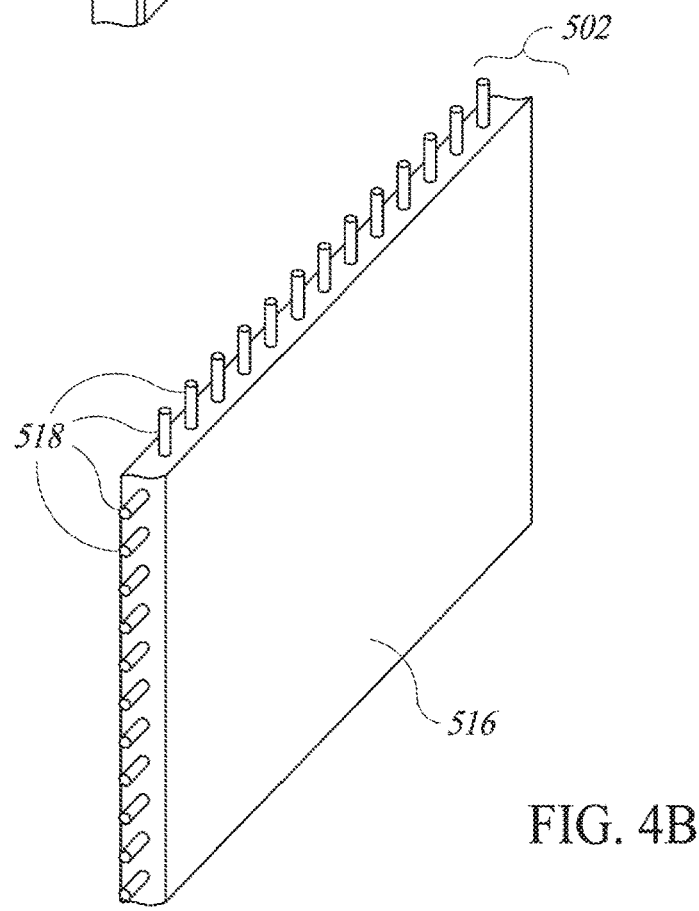
FIG. 4B is an isometric view of a portion of the shielded tote or shielded tray of FIGS. 3A and 3B, which, according to at least one illustrated implementation can include a packaging layer and a grid shield layer.

FIG. 3A shows a shielded tote or tray 500 in a sealed or closed configuration, according to at least one illustrated implementation. FIG. 3B shows the shielded tote or tray 500 in an unsealed or opened configuration, according to at least one illustrated implementation. FIG. 4A shows a cross-section portion of a shielded tote or tray 500 according to one illustrated embodiment. FIG. 4B shows a cross-section portion of a shielded tote or tray 500 according to another illustrated embodiment.

The shielded tote or tray 500 includes body 502 that defines an interior 504 (FIG. 3A) and an opening 506 to selectively provide access to the interior 504 from an exterior 508 of the shielded tote or tray 500. The shielded tote or tray 500 includes a selectively releasable or removable lid or cover 510, which is movable from a sealed or closed configuration (FIG. 3A) to an unsealed or open configuration (FIG. 3B). The lid or cover 510 can, for example, be releasable retained along a lip 512 (FIG. 3B) of the body 502 that surrounds the opening 506, for instance via a pressure sensitive adhesive.

As illustrated in FIGS. 3A and 3B, the body 502 may be formed of an electrically conductive material, for example a metal, for instance stainless steel. The lid or cover 510 can be formed of an electrically conductive material, for example a metal, for instance stainless steel, or more preferably a metal foil (e.g. aluminum foil, copper foil), or a metalized flexible substrate, for instance a metalized Mylar®, metalized paper polyethylene, metalized plastic laminate, cardboard, fiberboard, etc. The combination of the body 502 and the lid or cover 510 shield (e.g., Faraday cage) the contents of the shielded tote or tray 500 when in the sealed or closed configuration. Removal of the lid or cover 510 exposes the contents of the shielded tote or tray 500 to interrogation signals and allows responses to be sent.

Alternatively, as illustrated in FIG. 4A, the body 502 of the shielded tote or tray 500 can for example include one or more electrically conductive foil layers 514 laminated to a respective non-electrically conductive outer packaging layer or substrate (e.g., plastic, cardboard, fiberboard) 516.

Alternatively, as illustrated in FIG. 4B, the body 502 of the shielded tote or tray 500 can for example include one or more electrically conductive mesh or grid layers 518 laminated to or encased in a respective non-electrically conductive outer packaging layer or substrate (e.g., plastic, cardboard, fiberboard) 516.

The shielded tote or tray 500 can, for example, be closed via an adhesive or heat sealed along at least one edge. The contents can advantageously be loaded into and sealed in the interior 504 (FIG. 3B) of the shielded tote or tray 500 in a sterile environment. Alternatively, the contents can be sterilized while in the tote or tray 500, for instance after being hermetically seal via exposure to Gamma radiation and/or heat. The shielded tote or tray 500 may include a pull-tab 520, that facilitates opening, for example by releasing the lid or cover from the body.

The shielded tote or tray 500 may bear labeling 522 (FIG. 3A). The label 522 can, for example, include one or more human-readable pieces of information 524a, 524b (e.g., alpha-numeric text or legends). The label 522 can, for example, include one or more optically machine-readable pieces of information, for example one or more machine-readable symbols 526 (e.g., one-dimensional or barcode symbols, two-dimensional or matrix code symbols). The information in the human-readable pieces of information 524a, 524b and/or encoded in the machine-readable symbol(s) 526 can identify the contents of the shielded tote or tray 500 by name, quantity, manufacturer, and lot and/or batch number.

The shielded tote or tray 500 may bear one or more wireless communications transponders, for example an RFID transponder 528 and/or a dumb wireless transponder 530. The RFID transponder and/or dumb wireless transponders 528, 530 are preferably located on an exterior 428 of the shielded tote or tray 500 or at least exterior to a shield layer of the piece of shielded packaging 400. The RFID transponder and/or dumb wireless transponders 528, 530 can be retained via an adhesive or can be heat welded or RF welded to the piece of shielded packaging 400. The RFID transponders 528 can store and return information that identifies the contents of the shielded tote or tray 500 by name or description (e.g., 4×4 gauze), quantity (e.g., 10 pieces), manufacturer, lot and/or batch number, date of manufacture and/or expiration date.

The contents, for example absorbent surgical sponges, gauze and/or padding 532, may bear one or more wireless communications transponders, for example an RFID transponder 534a (only one called out in FIG. 3B) and/or a dumb wireless transponder 536a (only one called out in FIG. 3B). The RFID transponder and/or dumb wireless transponders 534a, 536a can be attached to an exterior surface or an inner surface (e.g., interior folded surface) of the surgical sponges, gauze and/or padding 532. The RFID transponder and/or dumb wireless transponders 534a, 536a can be retained via an adhesive, can be heat welded or RF welded to the surgical sponges, gauze and/or padding 532, stitched thereto by cotton or other thread or fiber, and/or clamped thereto via one or more fasteners (clamp, rivet, snap, staple). The structures and techniques disclosed in U.S. Patent Application Publication No. 2014/0303580 may be employed to secure the RFID transponder 534a and/or dumb wireless transponders 536a to the surgical sponges, gauze and/or padding 532. The RFID transponders 534a can store and return information that identifies the contents of the shielded tote or tray 500 by name, quantity, manufacturer, lot and/or batch number, date of manufacture and/or expiration date.

The contents, for example instruments 540, may bear one or more wireless communications transponders, for example an RFID transponder 534b (only one called out in FIG. 32B) and/or a dumb wireless transponder 536b (only one called out in FIG. 3B). The RFID transponder and/or dumb wireless transponders 534b, 536b can be attached to an exterior surface or an inner surface (e.g., interior folded surface) of the instruments 540. The RFID transponder and/or dumb wireless transponders 534b, 536b can be retained via an adhesive, can be a weld to the instruments 540, stitched or tied thereto by thread or wire, and/or clamped thereto via one or more fasteners (clamp, rivet, snap, staple). The structures and techniques disclosed in U.S. Pat. Nos. 7,898,420 and 8,354,931 may be employed to secure the RFID transponder and/or dumb wireless transponders 534b, 536b to the instruments 540.

The RFID transponders 534a, 534b can store and return information that identifies the particular item (e.g., absorbent surgical sponges, gauze and/or padding 532, instrument 540) to which the RFID transponder 534a, 534b is attached. The information can, for example, include a name or description of the item (e.g., 4×4 gauze, forceps), manufacturer, lot and/or batch number, date of manufacture and/or expiration date.

Figure 5:
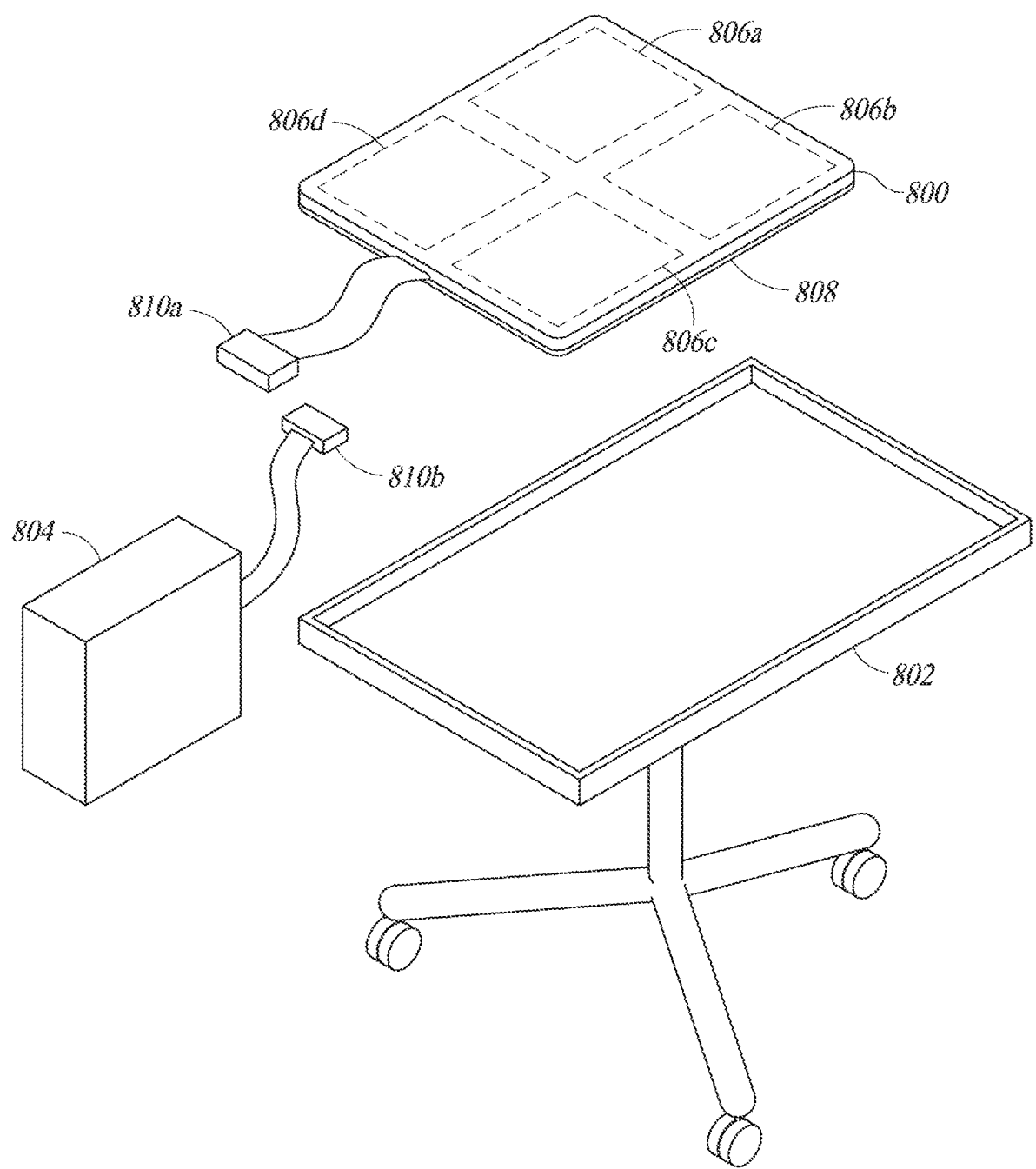
FIG. 5 is an isometric view of a pad or mat with one or more antennas according to one illustrated implementation, which can be used on a table or stand and communicatively coupled to an interrogator or reader to wirelessly read information from one or more wireless communications transponders attached to medical or clinical objects or items when carried on the table or stand.

FIG. 5 shows a mat 800, a table or stand 802 on which the mat 800 can be placed, and an RFID interrogator 804 that is communicatively coupleable to one or more antennas 806a-806d (four shown, collectively 806) physically coupled to or encased in the mat 800, according to at least one illustrated implementation.

The mat 800 houses or carries at least one antenna 806. Preferably, the antennas 806 are encased in the mat 800, which may be formed of an electrically non-conductive or electrically insulative material to prevent unintentional shorting of the antenna 806. One or more mats 800 may be positioned on or in the tables or stands 802 to position antennas 806 to interrogate items (e.g., instruments, supplies) carried on the mat 800. Additionally, one or more mats 800 may be located in or on a receptacle (not shown) to interrogate items (e.g., instruments, supplies) in the receptacle.

The mat 800 may take a variety of forms, and may be disposable, or may be capable of withstanding multiple cycles of sterilization (e.g., chemical, heat, radiation, etc.). The mat 800 or portions thereof may be electrically insulative. The mat 800 may be radiolucent, particular if the mat 800 is expected to be located between a patient and a radiological imaging source. The mat 800 may take a conventional form, for example cotton, open cell or a closed cell foam rubber, rubber or silicone, with or without a suitable cover. The mat 800 may optionally be detachably secured to the table or stand 802 via various fasteners, for instance ties, or hook and loop fastener commercially available under the trademark VELCRO®.

The antenna 806 may take a variety of forms, for instance a loop antenna, dipole antenna, slot antenna, etc. The antenna 806 may constitute an electrically conductive trace carried by the mat 800. For example, the antenna 806 may be carried on an outer surface of the mat 800 or carried in an interior of the mat 800, as illustrated in FIG. 5. The antenna 806 may be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) may be radiolucent. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

The mat 800 may optionally include an RF shield 808. The RF shield 808 may take a variety of forms, which provide directional RF shielding. For instance, the RF shield 808 may comprise an electrically conductive plate or wire mesh to form a partial Faraday cage. Such may be used to ensure that only selected areas are interrogated. For example, such can be employed to ensure that only sterile fields associated with the tables or stands 102, 104 (FIG. 1) on which the mats 800 are located are interrogated. Such may advantageously be employed to ensure that transponders located in the body of the patient are not interrogated or read. The RF shield 808 may be generally planar, or may have one or more raised portions, for example an upstanding peripheral lip or edge (not shown).

Alternatively, the table or stand 802 or a portion thereof may consist of a metal such as a sheet of metal or mesh of metal wires, which functions as an RF or Faraday shield, and thus constitutes an RF shield to shield against radio and microwave frequencies. In particular, metal (e.g., stainless steel) may be on an outer surface of the table or stand 802, may be a layer in the table or stand 802 or may constitute the entire table or stand 802. Consequently, the mat 800 itself omits an RF shield.

A wired connector 810a may provide communicative coupling of the antenna 806 with a complementary wire connector 810b of the RFID interrogator or reader 804. The wire connecters 810a, 810b may have a standard interface (e.g., USB connectors) to allow selective coupling and uncoupling to the RFID interrogator or reader 804 via one of the ports thereof. Appropriate instructions (e.g., software, firmware) may be loaded in response to the coupling of the antenna 806 to the RFID interrogator or reader 804. For example, instructions may be loaded to a control subsystem of the RFID interrogator or reader 804.

The RFID interrogator or reader 804 can, for example, be an integral to the mat 800, hence denominated as an integral RFID interrogator or reader.

The RFID interrogator or reader 804 may take a variety of forms, but will typically include a transmitter and/or receiver, which may be formed as a transceiver. The transmitter and/or receiver are communicatively coupled to the antenna 806 by electrically conductive paths. The RFID interrogator or reader 804 may be configured to transmit interrogation signals and receive response signals. The RFID interrogator or reader 804 may further be configured to decode information encoded in the response signals, for example unique identifiers that uniquely identify the wireless identification or RFID transponders, which are emitted or backscattered as response signals to interrogation signals. Alternatively, the RFID interrogator or reader 804 may send the commands to the wireless identification or RFID transponders to control operation of the wireless identification or RFID transponders. For example, RFID interrogator or reader 804 may implement a singulation algorithm, to allow reading of a plurality of wireless identification or RFID transponders in a group. For instance, the RFID interrogator or reader 804 may send an interrogation signal which includes a command, and thereby cause each wireless identification or RFID transponder that is read to stop responding for a period of time, allowing the signals of other wireless identification or RFID transponders to be detected and decoded. For instance, the RFID interrogator or reader 804 may transmit an interrogation signal in an environment, More than one wireless transponder may be respond. The RFID interrogator or reader 804 is typically capable of discerning one response amongst many. Some wireless identification or RFID transponders are operable to set a random delay time before responding to an interrogation signal, facilitating singulation. This prevents or reduces instances of collisions between the response signals from the various wireless transponders in range of an interrogation signal. In singulation, the RFID interrogator or reader 804 may uniquely identify the one wireless transponder based on a unique identifier encoded in its response signal. The RFID interrogator or reader 804 the transmits a signal with the unique identifier and with a command to salience the particular wireless transponder. While many wireless transponders may receive that signal, the one wireless transponder to which the signal is addressed (e.g., via the unique identifier) will execute the command. The command causes that wireless transponder to ignore further interrogation signals, for instance during a defined period of time. The RFID interrogator or reader 804 may iterate through this algorithm, in turn identifying and silencing all wireless transponders in its range. This may continue until, for example, no wireless transponders respond to an interrogation signal for a define period of time or to a defined number of instances of transmission of the interrogation signal.

Figure 6A:
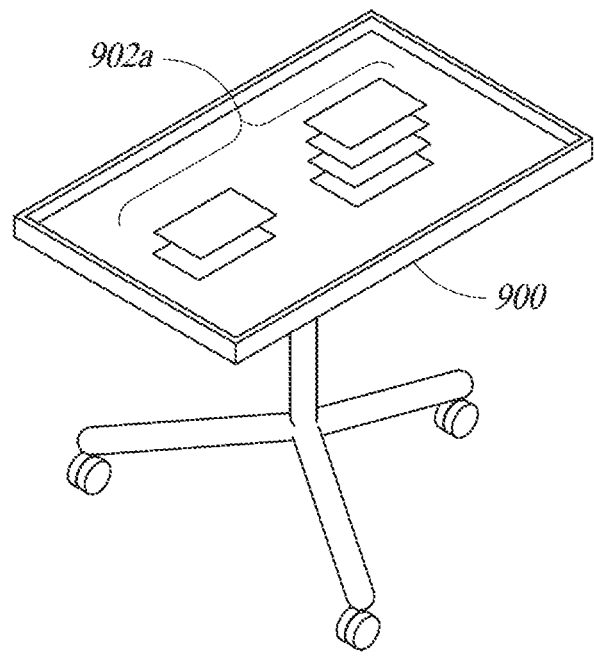
FIG. 6A is an isometric view of a pad or mat with one or more antennas, the pad or mat carried on a table or stand with a number of medical or clinical objects or items carried thereon, for example after or proximate an end of a medical or clinical procedure, according to at least one illustrated implementation.

FIG. 6A shows a first table or stand 900 with a number of supplies 902a for use in a medical or clinical procedure, according to at least one illustrated embodiment.

The first table or stand 900 may take any of a variety of forms, for example instrument tables, supply tables, Mayo stands or tables and/or back tables. Various supplies 902a are positioned on the first table, for example at or proximate a start of a medical or clinical procedure. Wireless identification or RFID transponders associated with the supplies are interrogated, and identifying information read and entered into a data store, for instance checked into an inventory database for the particular medical or clinical procedure. The wireless identification or RFID transponders may be interrogated using a handheld antenna, body-worn antenna, room antennas, or mat-based antenna.

Figure 6B:
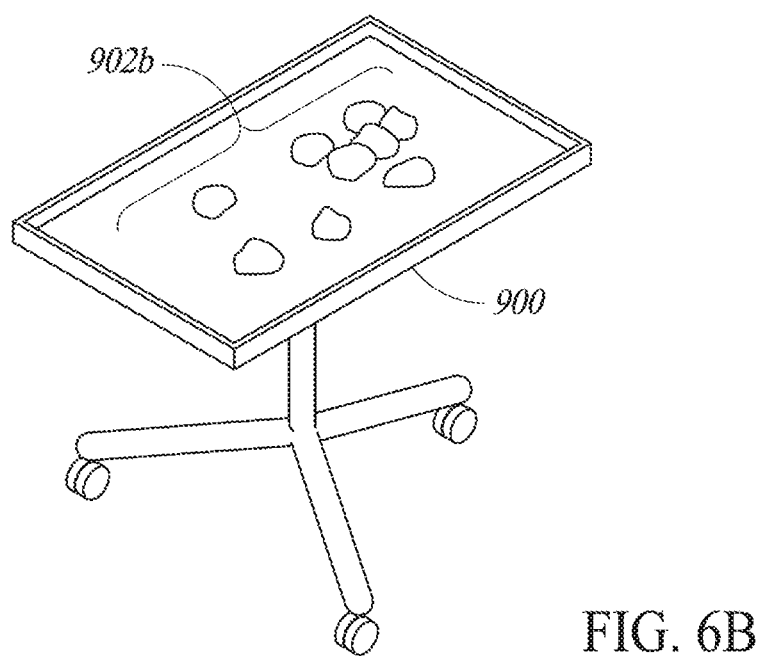
FIG. 6B is an isometric view of a pad or mat with one or more antennas, the pad or mat carried on a table or stand with a number of medical or clinical objects or items carried thereon, for example prior to or proximate a start of a medical or clinical procedure, according to at least one illustrated implementation.

FIG. 6B shows the first table or stand 900 with a number of supplies 902b which supplies have been used in a medical or clinical procedure, according to at least one illustrated embodiment.

Various used supplies 902b are positioned on the first table 900, for example at or proximate an end of a medical or clinical procedure. Wireless identification or RFID transponders associated with the supplies are interrogated, and identifying information read and entered into a data store, for instance checked out of an inventory database for the particular medical or clinical procedure. The wireless identification or RFID transponders may be interrogated using a handheld antenna, body-worn antenna, room antennas, or mat-based antenna. Notably, the same antenna and RFID interrogator can be used to interrogate the supplies on the first table or stand 900 at a first time (e.g., at or proximate a start of a medical or clinical procedure) and at a second time (e.g., at or proximate an end of a medical or clinical procedure).

FIG. 8A shows a trocar 1100 with one or more antennas 1102a, 1102b, 1102c, 1102d (four shown, collectively 1102), according to at least one illustrated implementation.

The trocar 1100 can take any of a large variety of forms, resembling or even being identical to existing trocars, with the addition of one or more antennas 1102. The trocar 1100 typically has a cannula 1104 with a first or proximal end 1106a and a second or distal end 1106b. As used herein, the term "distal" refers to that portion of a device that is farther from the user, while the term "proximal" refers to that portion of a device that is closer to the user. The cannula 1104 delineates a lumen 1108 through the cannula 1104 that extends from the proximal end 1106a to the distal end 1106b. A first or proximal port 1110a at the proximal end 1106a and a second or distal port 1110b at the second end 1106b provide access to an interior of the lumen 1108 from an exterior of the cannula 1104 or trocar 1100. The trocar 1100 typically includes one or more seals 1112, for example, at or proximate the proximal end 1106a of the cannula 1104. The seal(s) 1112 allows instruments to pass through the lumen 1108 of the cannula 1104 while preventing air from escaping from a bodily cavity. The trocar 1100 typically includes an obturator 1124 that movingly extends through the cannula 1104. The obturator 1124 may, for example, have a piercing tip at or proximate the distal end 1106b, that in operation pierces, slices or penetrates bodily tissue (e.g., skin) of a patient and thereby allows the cannula 1104 to penetrate bodily tissue.

The at least one trocar antenna 1102 is physically coupled to the trocar 1100, for example carried by the cannula 1104, and positioned and oriented to provide wireless communications coverage of at least a portion of an interior of the lumen 1108, including coverage of any wireless communications identification transponders (e.g., RFID transponders) that pass through the lumen 1108 of the cannula 1104. The at least one trocar antenna 1102 can, for example, be physically releasably or removably coupled to the trocar 1100. A range of the at least one trocar antenna 1102 should encompass the interior of the lumen 1108 at least at one cross-section of the lumen 1108 taken across the lumen, for instance perpendicular to a major, principal or longitudinal axis of the lumen 1108. The range can be an emission range, i.e., the effective range of an interrogation signal emitted by the trocar antenna 1102. The range can additionally or alternatively be a detection range, i.e., the effective range at which a response signal is detected via the trocar antenna 1102.

Each trocar antenna 1102 comprises at least one electrically conductive coil or band, for example a C-shaped band or an O-shaped band. The band may, for example be resilient, and may be made of metal (e.g., spring steel), or a plastic or other material. One or more additional fasteners (e.g., clamps, screws, nuts, bolts, adhesives) can be employed to secure (e.g., releasably secure) the trocar antenna 1102 to the trocar 1100. Release, detachment or removal of the trocar antenna 1102 from the trocar 1100 allows the trocar antenna to be sterilized and reused. In contrast, trocars 1100 are often single use disposable items. While sometimes referred to in the singular, some implementations can employ two or more trocar antenna 1102. Each trocar antenna 1102 may be separately attachable to and detachable from the trocar 1100, or may constitute a single integral unit attachable and detachable from the trocar 1100.

As illustrated, a first trocar antenna 1102a may, for example, be concentric with and located at or proximate the proximal port 1110a. As illustrated, a second trocar antenna 1102b may be concentric with and located at or proximate the distal port 1110b. Thus, the at least one trocar antenna 1102 can include a first trocar antenna 1102a positioned and oriented to provide coverage of the proximal port 1110a and all wireless communications identification transponders passing through the proximal port 1110a, and at least a second trocar antenna 1102b positioned and oriented to provide coverage of the distal port 1110a and all wireless communications identification transponders passing through the distal port 1110b. Optionally, a third trocar antenna 1102c may, for example, be concentric with and located at or proximate the proximal port 1110a spaced longitudinally with respect to the first trocar antenna 1102a. Optionally, a fourth trocar antenna 1102d may, for example, be concentric with and located at or proximate the distal port 1110b, spaced longitudinally with respect to the first trocar antenna 1102a. The longitudinal spacing of the trocar antenna 1102 may facilitate determination of a direction of travel of an object through the lumen 1108 of the cannula 1104. For example, detection of successive passage past respective trocar antennas can advantageously indicate whether an object is moving from the proximal end toward the distal end, or conversely from the distal end toward the proximal end. Discrete circuitry and/or a suitably programmed microprocessor in the interrogator, or remote from and responsive to output of the interrogator, can determine direction, for instance based on timing of a sequence of detection events produced by passage of an object past one or more trocar antennas 1102. Alternatively or additionally, the discrete circuitry or programmed microprocessor may determine direction from a frequency of the response signal, for example taking into account a Doppler shift as an object moves relatively towards and away from one or more trocar antennas 1102.

An interrogator or reader 1114 (e.g., RFID interrogator or reader, dumb wireless transponder interrogator) and associated antenna 1116 can be physically coupled to the trocar 1100, and communicatively coupled to the trocar antenna(s) 1102. Alternatively, the trocar 1100 can include one or more transmitters and associated antennas to wirelessly communicatively couple the trocar antenna(s) 1102 to an external interrogator or reader (e.g., RFID interrogator or reader, dumb wireless transponder interrogator). Alternatively, the trocar 1100 can include one or more electrical cables and connectors (e.g., plug) to detachably communicatively couple the at least one trocar antenna to an external interrogator or reader. The interrogator or reader 1114 can, for example, be physically releasably or removably coupled to the trocar 1100, for instance via one or more bands, clamps or other fasteners. Release, detachment or removal of the interrogator or reader 1114 from the trocar 1100 allows the trocar antenna to be sterilized and reused.

The interrogator or reader 1114 is operable to cause the trocar antenna(s) 1002 to emit interrogation signals (e.g., radio or microwave frequencies), and to detect response signals from any exposed wireless communications identification transponders that pass through the lumen of the cannula 1104, preferably without detecting any wireless communications identification transponders that are outside the interior of the lumen.

In some implementations, the trocar 1100 may be a shielded trocar. In particular, the cannula 1104 of the trocar 1100 may shield the trocar antenna(s) 1102 from response signals emitted by any wireless communications identification transponders or other antennas located in externally with respect to the interior of the lumen 1108 of the cannula 1104 of the trocar 1100, as well as from radio frequency or microwave frequency noise in the ambient environment external to the lumen 1108 of the cannula 1104. For example, the cannula 1104 of the trocar 1100 may be electrically conductive, for example comprising a metal, for instance stainless steel.

The trocar 1100 may include one or more switches or sensors positioned and/or oriented to detect the presence or passage of one or more tagged items, and communicatively coupled to provide a trigger signal to cause the interrogator or reader 1114 to cause interrogations signals to be sent. The switch or sensor can take any of a large variety of forms, for example a Reed switch, an optical emitter (e.g., infrared LED) and sensor pair, a mechanical switch, slide switch, push button switch, contact switch, inductive sensor, etc. The switch or sensor can be fixed to the trocar 1100, or may be removably or releasably secured thereto via one or more bands, clamps, or other fasteners. Release, detachment or removal of the switch or sensor from the trocar 1100 allows the switch or sensor to be sterilized and reused. The switch or sensor employ wired communications or may include a radio (e.g., Bluetooth® radio) to provide for wireless communications.

FIG. 8B shows a portion of a trocar 1100a similar to that of FIG. 8A, and including an RF shield 1120 encased between two electrically non-conductive layers 1122a, 1122b, according to at least one illustrated implementation.

The RF shield 1120 can comprise an electrically conductive material, for example a metal. The RF shield 1120 can comprise an electrically conductive sheath, for instance an electrically conductive sheet of material, or an electrically conductive mesh or grid. The two electrically non-conductive layers 1122a, 1122b can, for example, comprise a plastic. The two electrically non-conductive layers 1122a, 1122b can each be made of different materials from one another. The trocar antenna(s) 1102 (FIG. 8A) can, for example, be encased in the plastic of the cannula 1104.

FIG. 8C shows a portion of a trocar 1100b similar to that of FIG. 8A, and including an RF shield 1120 lining an inner wall formed by an outer electrically non-conductive layer 1122, according to at least one illustrated implementation.

The RF shield 1120 can comprise an electrically conductive material, for example a metal. The RF shield 1120 can comprise an electrically conductive sheath, for instance an electrically conductive sheet of material, or an electrically conductive mesh or grid. The electrically non-conductive layer 1122 can, for example, comprise a plastic.

Figure 9:
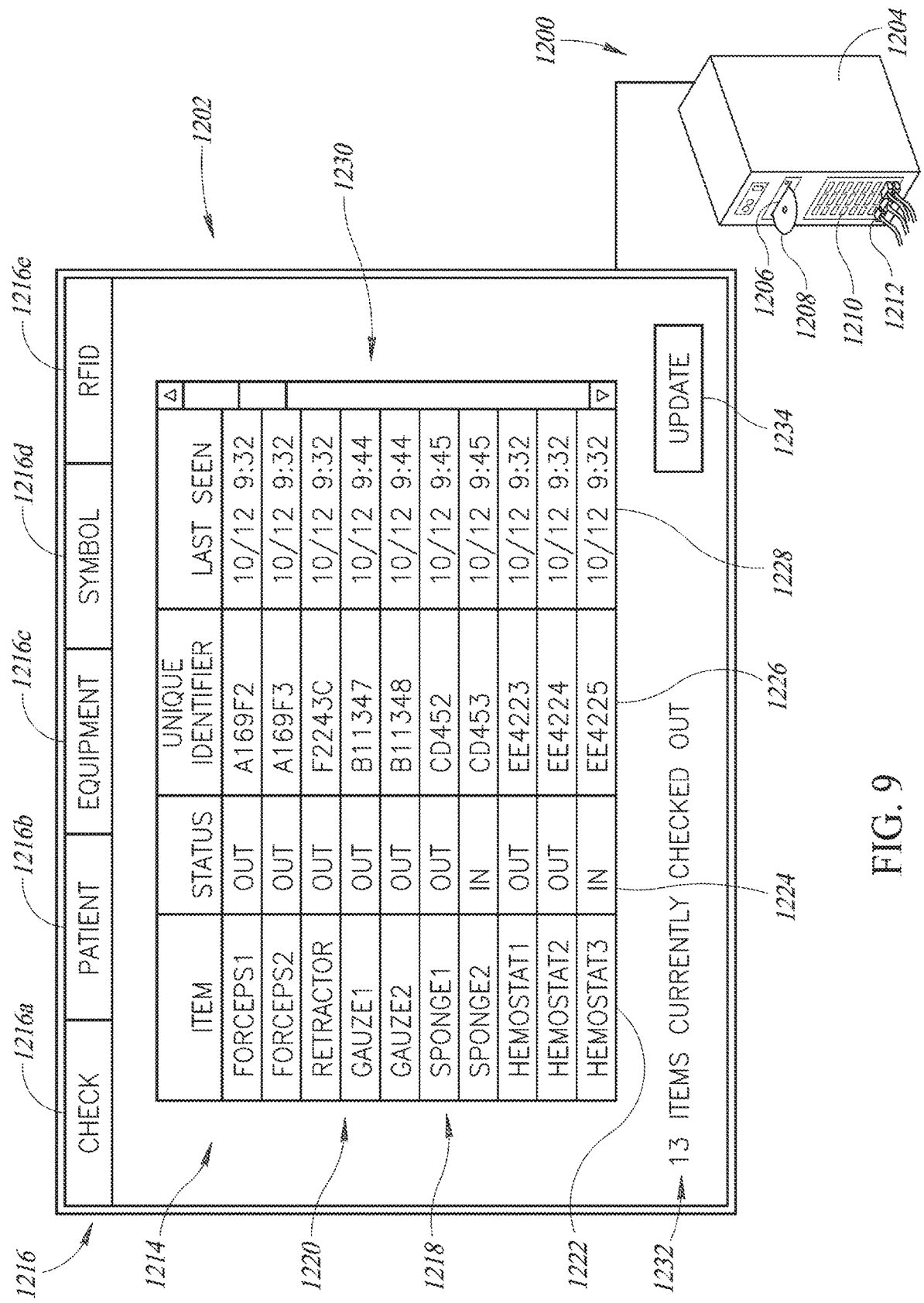
FIG. 9 is a front elevation view of an accounting system and display of the accounting system of FIG. 1, according to one illustrated embodiment.

FIG. 9 shows an accounting system 1200 and display 1202, according to one illustrated embodiment.

The accounting system 1200 may include a housing 1204 which houses one or more microprocessors, memory (e.g., RAM, ROM, FLASH), nontransitory computer- or processor-readable storage devices (e.g., hard disk drive, solid state drive), and buses (e.g., power bus, communications buses). The accounting system 1200 may include one or more slots 1206 or other receptacles to receive computer- or processor-readable media 1208, for instance spinning media (e.g., compact disks, DVDs), fixed media (e.g., Flash cards, secure digital (SD) cards, multimedia (MM) cards). The accounting system 1200 may also include one or more ports or connectors 1210 (only one called out in FIG. 9) to allow selective connection and disconnection of various devices to the control subsystem of the presence/absence interrogator or reader 1200. The connection may provide communications and/or power between the accounting system 1200 and various connected devices. Devices may take a variety of forms, for instance one or more radio frequency identification (RFID) interrogation systems 120a (FIG. 1), one or more wireless presence/absence interrogation systems 122 (FIG. 1), one or more computers or terminals 128 (FIG. 1), one or more antennas 142, 146 (FIG. 1), and any other device capable of transmitting or receiving data and/or instructions or capable of any other form of communications. Such ports or connectors 1210 may take the form of various industry standard ports or connectors, for example Universal Serial Bus ports. While illustrated as physical ports to couple with a connector or plug 1212 (only one called out in FIG. 9), the ports 1210 may take the form of one or more wireless transmitters, receivers or transceivers. Such may, for instance be compatible with various industry standards, for instance 802.11b, 802.11c, 802.11n, or BLUETOOTH®. Various interfaces may provide access to remote services, such as the Internet or "cloud" storage, or to other computing devices.

The display 1202 may be any screen or monitor suitable to display information and/or a user interface (e.g., graphical user interface). The display 1202 may, for example take the form of an LCD display panel or a CRT display. The display 1202 may be a standalone, separate piece of equipment. Alternatively, the display 1202 may be integrated into the housing 1204 of the accounting system 1200.

Figure 10:
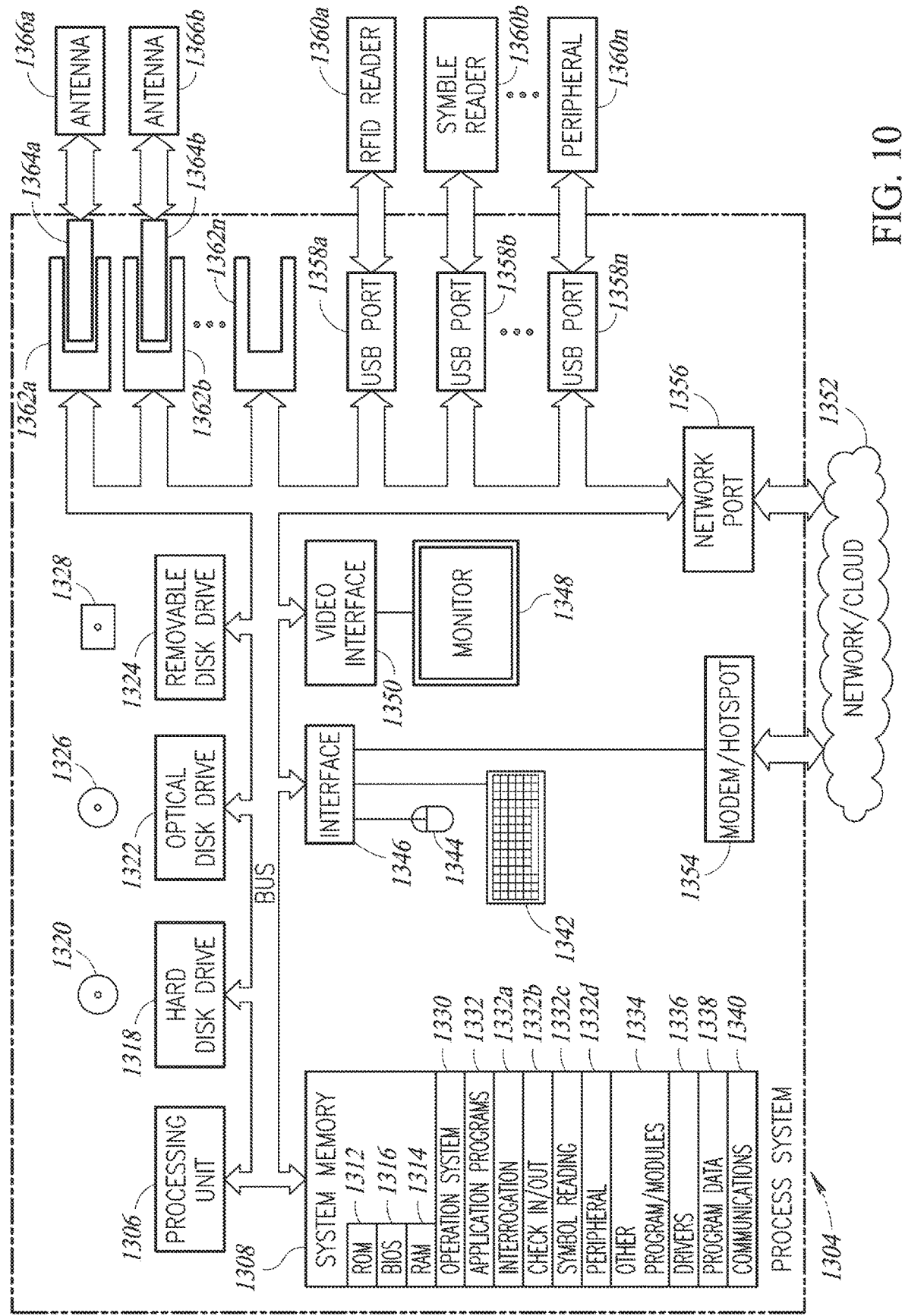
FIG. 10 is a schematic diagram of a control subsystem according to one illustrated embodiment, the control subsystem including a processor system, plug-in boards and various ports to provide communications with antennas, readers and various non-reader peripheral devices or equipment.

The display 1202 is communicatively coupled to the processor-based system 1304 (FIG. 10). The processor-based system 1304 (FIG. 10) is configured to control the images displayed on the display 1202. The display 1202 may provide all, or a portion, of a user interface, for an end user to interact with the microprocessors, memory, nontransitory computer- or processor-readable storage devices. The display 1202 may take the form of a touch panel display, allowing an end user to enter commands or instructions, or otherwise make selections, via a graphical user interface 1214. Alternatively, or additionally, one or more other user input devices may be provided, for instance a keyboard, keypad, mouse, trackball, other pointer control device, or a microphone and voice activated interface.

The graphical user interface 1214 may include one or more menus 1216. The menus 1216 may include icons 1216a-1216e corresponding to specific functions or operational modes which may be selected. A specific function or mode may be selected by touching the appropriate portion of the user interface or placement of a cursor over the appropriate portion of the user interface. In response, a set of related icons may be displayed for instance by way of a pull-down menu or dialog box. Such may allow further selections or configuration of the specific mode or function. Icons 1216a-1216e for some exemplary functions or operational modes are illustrated. Selection of a checking function or mode 1216a causes the accounting system 1200 to check medical procedure related instruments and supplies in and out in a database. Selection of a patient function or mode icon 1216b may allow patient-specific information to be viewed and/or recorded or modified. Selection of an equipment function or mode 1216c may allow the end user to read information or data produced or collected by various pieces of medical equipment on the display 1202, for instance, blood pressure, heart rate, temperature, blood oxygen levels, respiration, electrocardiogram, etc. The equipment function or mode may additionally, or alternatively, allow an end user to configure parameters of a piece of medical equipment via the user interface. Selection of the symbol reading function or mode icon 1216d may allow use of a machine-readable symbol reader (not shown in FIG. 9), while the selection of the RFID reading function or mode icon 1216e may allow the use of an RFID interrogator or reader 140 (FIG. 1) or presence/absence interrogation system(s) 122 (FIG. 1).

The graphical user interface 1214 may have one or more windows or panels 1218 (only one illustrated) that present or display information. Multiple windows or panels 1218 may be displayed at the same time, or individual windows or panels 1218 may be displayed one by one, for example in response to a user selection of a particular function or mode or selection of a particular window or panel 1218.

The illustrated window or panel 1218 is related to a medical procedure related object accounting mode or function that checks medical procedure related instruments and supplies in and out in a data store (e.g., database) stored in at least one computer- or processor-readable storage medium, hence is also denominated as a checking mode or function.

In the accounting or checking mode or function, the accounting system 1200 determines which medical procedure related instruments 108 (FIG. 1) and supplies 110 (FIG. 1) are present in at least some portions (e.g., unshielded portions, shielded portions) of medical or clinical environment 300 just prior to or at a start of a medical or clinical procedure. The accounting system 1200 also determines which medical procedure related instruments 108 and supplies 110 are present in at least some portions (e.g., unshielded portions, shielded portions) of medical or clinical environment 300 just prior to or at an end a medical or clinical procedure. The accounting system 1200 may optionally determine which medical procedure related instruments 108 and supplies 110 are present in at least some portions (e.g., unshielded portions, shielded portions) of medical or clinical environment 300 at intervals during the medical procedure between the start and the end of the medical or clinical procedure, for example from time to time, periodically or even continuously. The accounting system 1200 may make such determinations based, for example, on unique identifiers read from one or more RFID transponders by one or more RFID interrogators or readers 140 (FIG. 1).

As previously noted, the RFID interrogator(s) or reader(s) 140 can transmit interrogation signals from one or more antennas 146 (FIG. 1), to excite, power or otherwise cause wireless communications identification or RFID transponders 124b (FIG. 1) to transmit or emit a response signal. One or more antennas 146 may receive the response signals from the excited or powered RFID transponders 124b. The RFID interrogator(s) or reader(s) 140 and/or the accounting system 1200 may decode the received response signals to determine identifying information encoded therein. The RFID interrogator(s) or reader(s) 140 and/or the accounting system 1200 may logically associate each RFID transponder 124b with an item (e.g., instrument 108, supply 110) to which the respective RFID transponder 124b is physically attached.

The accounting system 1200 may catalog the medical or clinical procedure related instruments 108 and supplies 110 that are present based on the identifying information. For example, the response signals may contain unique identifiers stored or hardcoded into the RFID transponders 124b. These unique identifiers may be mapped to information about the respective instruments 108 and/or supplies 110, for instance in a data store (e.g., database). Alternatively, information about the respective instruments 108 and/or supplies 110 may be stored in the transponder and encoded in the response signals. Such information may include the name or identity of the instrument 108 or supply 110, a manufacturer identification, model identification, date put in use, date refurbished or sharpened, date sterilized, method of sterilization, history of use, etc. Such allows tracking and/or tracking of instruments 108 and supplies 110, before, during and after use.

The accounting system 1200 may display information related to the status of the various instruments 108 and/or supplies 110 in a chart 1218 or other format. For example, the chart 1218 may include an entry, for instance a row 1220 (only one called out in FIG. 9), for each instrument 108 and supply 110 present proximate a start of the medical procedure. The instrument 108 or supply 110 may be identified by an identifier 1222, for instance a non-unique commonly recognized name or description. A current status of the instrument 108 or supply 110 may be identified by an appropriate status indicator 1224 (e.g., In/Out, Present/Absent). Optionally, a unique identifier associated with the instrument 108 or supply 110 may be identified by an appropriate indicator 1226 (e.g., unique identifier provided by an RFID transponder physically attached to the instrument 108 or supply 110). Optionally, "last seen" information identifying a time and date that the instrument 108 or supply 110 was last identified may be provided via an appropriate indicator 1228 (e.g., October 12 at 9:32 AM). A scroll bar 1230 or similar graphical user interface tool may be provided to allow a user to review information for a large number of instruments 108 and supplies 110.

The accounting system 1200 may determine if there is a discrepancy between the medical or clinical procedure related objects that were present at or proximate a start and at or proximate an end of the medical or clinical procedure. The accounting system 1200 may provide a suitable warning or notification 1232 if a discrepancy exists, and/or if a discrepancy does not exist. While illustrated as a visual notification, an aural and/or tactile notification may additionally or alternatively be supplied.

The graphical user interface 1214 may include one or more icons 1234 (only one illustrated), user selection of which may cause certain actions. For instance, selection of an update icon 1234 may cause the accounting system 1200 to cause a rescan or re-interrogation of the medical or clinical procedure environment 300, or portions thereof, to account for the presence, absence or location of various medical or clinical procedure related instruments 108 and tools 110.

FIG. 10 and the following discussion provide a brief, general description of a suitable processor system 1304 in which the various illustrated embodiments, as well as other embodiments can be implemented. The processor system 1304 can for example implement the wireless presence/absence interrogation systems 122 (FIG. 1). Additionally, or alternatively, processor system 1304 can for example implement the accounting system 130 (FIG. 1), 1200 (FIG. 9). Although not required, some portion of the embodiments will be described in the general context of computer-executable instructions or logic, such as program application modules, objects, functions, procedures or macros being executed by a computer or processor. Those skilled in the relevant art will appreciate that the illustrated embodiments as well as other embodiments can be practiced with other computer- or processor-based system configurations, including handheld devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processor-based devices, which are linked through a communications network. In a distributed computing environment, program modules may be located in local and/or remote memory storage devices, for instance in the cloud. Network connections allow for cloud computing and/or cloud storage.

The processor system 1304 may take the form of a conventional personnel computer (PC), which includes one or more processors 1306, system memories 1308 and system buses 1310 that couple various system components including the system memory 1308 to the processor 1306. The processor system 1304 and its components will at times be referred to in the singular herein, but this is not intended to limit the embodiments to a single system or single components, since in certain embodiments, there will be more than one system or other local or remote networked computing device or multiple instances of any component involved. Unless described otherwise, the construction and operation of the various blocks shown in FIG. 10 are of conventional design. As a result, such blocks need not be described in further detail herein, as they will be understood by those skilled in the relevant art.

The processor 1306 may be any logic processor, such as one or more central processor units (CPUs), microprocessors, digital signal processors (DSPs), application-specific integrated circuits (ASICs), field programmable gate arrays (FPGAs), etc.

As described in applicant's prior applications, the processor 1306 may take the form of a soft processor core, such as that supplied by XILINX under the name MICROBLAZE™, which implements a 32-bit processor including memory caches and a floating point unit. A soft core processor is one that is implemented by interconnected FPGA logic cells instead of by a traditional processor logic. The processor core may be connected to the internal FPGA peripherals using a 32-bit processor bus called the On-Chip Peripheral Bus. The XILINX supplied peripherals for the MICROBLAZE™ processor core include external memory interfaces, timers, and general purpose I/O. Custom logic to create the transmit signals, sample the ADC, and accumulate the transponder return signals may be designed as a peripheral to the soft processor core. The custom logic may be part of the design of the FPGA.

Alternatively, the processor 1306 may take the form of a full microprocessor. Non-limiting examples of commercially available microprocessors include, but are not limited to, an 80×86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. For example, the processor 1306 may take the form of a full microprocessor such as the ATOM™ processor, commercially available from Intel Corporation. The full microprocessor may be communicatively coupled to multiple analog antenna channels, for example via one or more plug-in boards 1364a, 1364b (collectively 1364, only two shown) which carry respective FPGAs and one or more suitable buses. The FPGA may, for example, act as a co-processor and/or cache. For example, the plug-in boards 1364 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which Patent Applications are incorporated herein by reference in their entirety.

The system bus 1310 can employ any known bus structures or architectures, including a memory bus with memory controller, a peripheral bus, and a local bus. A relatively high bandwidth bus architecture may be employed. For example, a PCI express™ or PCIe™ bus architecture may be employed, rather than an ISA bus architecture. Suitable FPGAs may include those from ATMEL Corporation. Such FPGAs may advantageously have built in PCIe bus architecture, allowing easy integration. This approach may enable more I/O ports, such as USB ports, may provide more or better video options, and may provide faster data rates from the analog antenna channels than otherwise possible using the ISA bus architecture and a soft processor core approach. Some embodiments may employ separate buses for data, instructions and power.

The system memory 1308 includes read-only memory ("ROM") 1312 and random access memory ("RAM") 1314. A basic input/output system ("BIOS") 1316, which can form part of the ROM 1312, contains basic routines that help transfer information between elements within the processor system 1304, such as during start-up.

The processor system 1304 also includes a hard disk drive 1318 for reading from and writing to a magnetic hard disk 1320, an optical disk drive 1322 for reading from and writing to removable optical disks 1326, and a removable disk drive 1324 for reading from and writing to removable disks 1328. The optical disk 1326 can be a CD or a DVD, etc., while the removable magnetic disk 1328 can be a magnetic floppy disk or diskette. The hard disk drive 1318, optical disk drive 1322 and removable disk drive 1324 communicate with the processor 1306 via the system bus 1310. The hard disk drive 1318, optical disk drive 1322 and removable disk drive 1324 may include interfaces or controllers (not shown) coupled between such drives and the system bus 1310, as is known by those skilled in the relevant art. Additionally or alternatively, the processor system 1304 may include one or more solid state drives (SSD). The drives 1318, 1322, 1324, and their associated computer-readable media 1320, 1326, 1328, provide nonvolatile storage of computer-readable instructions, data structures, program modules and other data for the processor system 1304. Although the depicted processor system 1304 employs hard disk 1320, optical disk 1326 and removable disk 1328, those skilled in the relevant art will appreciate that other types of computer-readable media that can store data accessible by a computer may be employed, such as magnetic cassettes, flash memory cards, Bernoulli cartridges, RAMs, ROMs, smart cards, etc.

Program modules can be stored in the system memory 1308, such as an operating system 1330, one or more application programs 1332, other programs or modules 1334, drivers 1336 and program data 1338.

The application programs 1332 may, for example, include interrogation logic 1332a, check in/out logic 1332b, and machine-readable symbol reading logic 1332c, as well as another other peripheral logic 1332d associated with operating a non-reader device, referred to in FIG. 10 and elsewhere herein as peripheral logic and peripheral device, respectively. The logic 1332a-1332d may, for example, be stored as one or more executable instructions. The interrogation logic 1332a may include logic or instructions to cause antenna(s) 142 (FIG. 1) and/or RFID interrogator(s) 140 (FIG. 1) to transmit wireless interrogation signals, receive response signals to the interrogations signals, and in the case of RFID transponders decode information encoded in the response signals, for instance unique identifiers stored in RFID transponders. Such may encode information in the interrogation signals, for instance information to be encoded in an RFID transponder. The check in/out logic 1332*b* may include logic to monitor or track a status of various medical procedure instruments and supplies. Such may, for example, update information in a data store (e.g., database) stored on one or more computer- or processor-readable storage media. Such may also allow the generation of queries and retrieval of information from such data store. Such may, for example, update create a record or field in the database for each medical procedure instrument or supply that is present in at least unshielded portions of the medical or clinical environment 300 (FIG. 1) before or at the start of a medical procedure. Such may also, for example, update a respective record or field of the data store or database if a medical procedure instrument or supply is removed from at least unshielded portions of the medical or clinical environment 300 (FIG. 1). Such may also, for example, update a respective record or field of the data store or database if the medical instrument or supply reappears in at least unshielded portions of the medical or clinical environment 300 (FIG. 1) during the medical or clinical procedures.

Such may take the form of identifying a particular instrument as being checked in if detected in at least unshielded portions of the medical or clinical environment 300 (FIG. 1), and otherwise identifying the particular instrument as checked out. A query may be run, either from time to time or before ending a medical or clinical procedure, to ensure that all the medical or clinical instruments and supplies present at the start of the medical or clinical procedure are present and accounted for at the end of the medical procedure. In some implementations, all instruments and supplies are placed in shielded portions (e.g., shielded receptacles) at or proximate the end of the medical or clinical procedure, and the medical or clinical environment is interrogated to determine that no response signals are received. This ensures that no medical instruments or supplies are left behind in a body of a patient undergoing a medical or clinical procedure.

The machine-readable symbol reading logic 1332*c* may allow the capture and decoding of information encoded in machine-readable symbols, such as barcode symbols, area or matrix code symbols and/or stacked code symbols. Such logic is commonly found in dedicated machine-readable symbol readers. The peripheral logic 1332*d* can be any logic loaded into or otherwise stored in a computer- or processor-readable storage medium. The peripheral logic 1332*d* allows operation of a peripheral device, such as a non-reader type device. For instance, the peripheral logic 1332*d* may collect data from one or more pieces of medical procedure equipment (e.g., cautery equipment, heart-lung machine, ablation system, anesthesia deliver apparatus) or medical procedure sensors (e.g., electrode, pulse-oximetry sensor, blood pressure sensor, temperature probe, heart monitor), or other data collection devices. Interrogation logic 1332*a*, machine-readable symbol reading logic 1332*c*, and/or peripheral logic 1332*d* may be automatically loaded into one or more computer- or processor-readable storage medium in response to the communicative coupling of a respective device to the presence/absence interrogator or reader 1360*a*, 1360*b*. Such may advantageously provide plug and play functionality for a wide variety of devices.

The system memory 1308 may also include communications programs 1340, for example a server and/or a Web client or browser for permitting the processor system 1304 to access and exchange data with other systems such as user computing systems, Web sites on the Internet, corporate intranets, extranets, or other networks as described below. The communications programs 1340 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document or to format information. A number of servers and/or Web clients or browsers are commercially available such as those from Mozilla Corporation of California and Microsoft of Washington.

While shown in FIG. 10 as being stored in the system memory 1308, the operating system 1330, application programs 1332, other programs/modules 1334, drivers 1336, program data 1338 and server and/or browser 1340 can be stored on the hard disk 1320 of the hard disk drive 1318, the optical disk 1326 of the optical disk drive 1322 and/or the magnetic disk 1328 of the magnetic disk drive 1324. A user can enter commands and information into the processor system 1304 through input devices such as a touch screen or keyboard 1342 and/or a pointing device such as a mouse 1344. Other input devices can include a microphone, joystick, game pad, tablet, scanner, biometric scanning device, etc. These and other input devices are connected to the processor 1306 through an interface 1346 such as a universal serial bus ("USB") interface, Firewire, and/or optical Firewire interface, that couples to the system bus 1310, although other interfaces such as a parallel port, a game port or a wireless interface or a serial port may be used. A monitor 1348 or other display device is coupled to the system bus 1310 via a video interface 1350, such as a video adapter. Although not shown, the processor system 1304 can include other output devices, such as speakers, printers, etc.

The processor system 1304 operates in a networked environment using one or more of the logical connections to communicate with one or more remote computers, servers and/or devices via one or more communications channels, for example, one or more networks 1352. These logical connections may facilitate any known method of permitting computers to communicate, such as through one or more LANs and/or WANs, such as the Internet, intranet, cloud, and/or extranet. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a WAN networking environment, the processor system 1304 may include a modem or wireless hotspot 1354 for establishing communications over a WAN, for instance the Internet. The modem 1354 is shown in FIG. 10 as communicatively linked between the interface 1346 and the network 1352. Additionally or alternatively, another device, such as a network port 1356, that is communicatively linked to the system bus 1310, may be used for establishing communications over the network 1352.

One or more interfaces or ports 1358*a*-1358*n* (collectively 1358, only three illustrated) that are communicatively linked to the system bus 1310, may be used for establishing communications over a WAN, LAN, parallel or serial cable, AC wiring (e.g., ZigBee® protocol transceiver), or wirelessly (e.g., WI-FI® radio, Bluetooth® radio). In some embodiments, the interfaces or ports 1358 may take the form of USB ports allowing communication via respective USB cables. Such may allow a variety of equipment to communicate with the processor system 1304. For example, such may allow communicative coupling with one or more RFID interrogators or readers 1360a, machine-readable symbol readers 1360b (e.g., machine-readable symbol scanners or imagers), and peripheral equipment 1360n (collectively 1360, only three illustrated). The readers 1360a, 1360b may be configured to transmit pre-processed information to the processor system 1304, for instance identifiers read from RFID transponders or optical symbols (e.g., printed or inscribed markings). The processor system 1304 may be configured to use such information. For instance, the processor system 1304 may be configured to check medical procedure instruments and supplies in and out in the database based on identifiers reader by the readers 1360a, 1360b. Additionally, or alternatively, the processor system 1304 may be configured to control or otherwise send instructions and/or data to the readers 1360a. 1360b. Likewise, the processor system 1304 may be configured to check medical procedure instruments and supplies in and out in the database based on information received from the peripheral equipment 1360c. Additionally, or alternatively, the processor system 1304 may be configured to control or otherwise send instructions and/or data to the peripheral equipment 1360c.

One or more interfaces or slot connectors 1362a-1362n (collectively 1362, only three illustrated) may allow the communicative coupling of plug-in boards 1364a, 1364b (collectively 1364, only two illustrated) to the processor system 1304. There may, for example, be one plug-in board 1362 for each antenna 1366a, 1366b (collectively 1366, only two illustrated, each of the antennas 1366 and plug-in boards 1364 constituting a separate channel. The slot connectors 1362 may allow expansion or use with different antenna configurations. The plug-in boards 1364 may each carry one or more circuits (e.g., analog and/or digital circuit components) configured to transmit interrogation signals from the respective antenna 1366 and to monitor the antenna 1366 for responses to the interrogation signals. For example, the plug-in boards 1364 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which Patent Applications are incorporated herein by reference in their entirety. Processor system 1304 may automatically recognize and be configured in response to a plug-in board 1364 being coupled to an interface or slot connector 1362, for example in a fashion similar to the coupling of a USB device to a computer system.

The processor system 1304 may include one or more synchronization circuits or logic (not shown) configured to control and synchronize the operation of the various plug-in boards 1364. The synchronization circuit or logic may be configured to cause one of the plug-in boards 1364 to transmit an interrogation signal from a first antenna, and cause one or more of the other plug-in boards 1364 to monitor for a response by a transponder to the interrogation signal. For instance, the synchronization circuit or logic may cause the plug-in boards 1364 to monitor all of the antennas 1366 for a response to the interrogation signal. Alternatively, the synchronization circuit or logic may cause the plug-in boards 1364 to have all of the antennas 1366 other than the antenna that transmitted a most recent interrogation signal monitor for a response. Such may advantageously allow monitoring sooner than would otherwise be possible since such can avoid the need to allow the transmitting antenna to return to a quiescent state after transmitting before monitoring for a response. The synchronization circuit or logic may synchronize the plug-in boards 1364 to successively cause the various antennas to transmit, for example starting with an antenna at one end, and successively transmitting from each of the antennas in a defined order. As a further alternative, the synchronization circuit or logic may synchronize the plug-in boards 1364 to cause the transmission of interrogations signals from a subset of the total set of antennas. While illustrated as removably coupled to the processor system 1304, the plug-in boards 1364 could be an integral unitary part thereof. For example, the various antennas may be controlled by respective circuits integrated into a signal circuit board. Alternatively, the various antennas may be controlled by a single circuit. While sequential interrogation is described, some implementations may employ parallel interrogation. Whether sequential or parallel interrogation is employed, the processor system 1304 may employ serial or parallel processing of information.

In a networked environment, program modules, application programs, or data, or portions thereof, can be stored in a server computing system (not shown) or in the cloud. Those skilled in the relevant art will recognize that the network connections shown in FIG. 10 are only some examples of ways of establishing communications between computers, and other connections may be used, including wirelessly.

For convenience, the processor 1306, system memory 1308, network port 1356, interface 1346, interfaces or ports 1358 and connector slots 1362 are illustrated as communicatively coupled to each other via the system bus 1310, thereby providing connectivity between the above-described components. In alternative embodiments of the processor system 1304, the above-described components may be communicatively coupled in a different manner than illustrated in FIG. 10. For example, one or more of the above-described components may be directly coupled to other components, or may be coupled to each other, via intermediary components (not shown). In some embodiments, system bus 1310 is omitted and the components are coupled directly to each other using suitable connections.

Figure 11A:
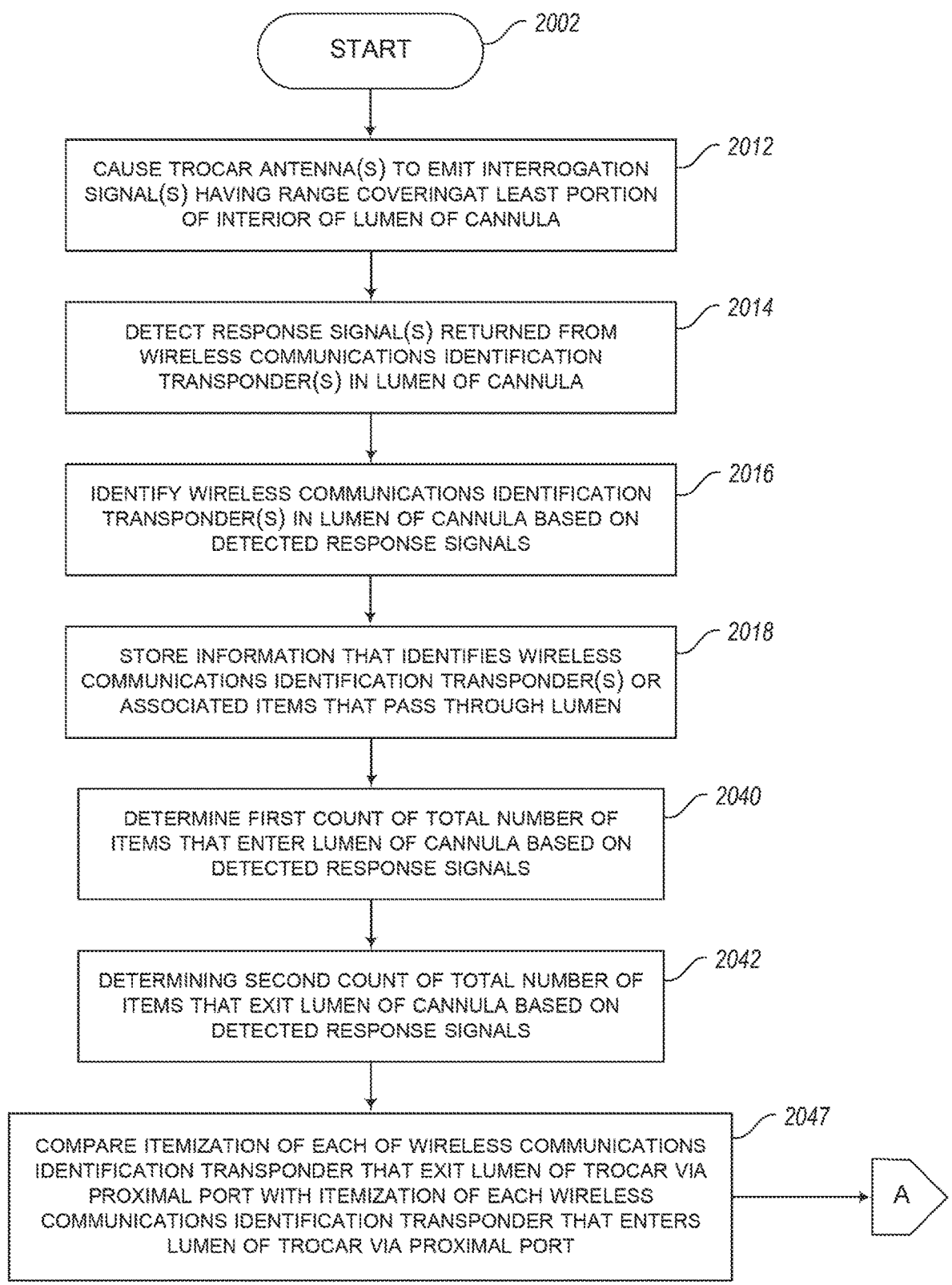
FIGS. 11A-11B are a flow diagram showing a workflow or method of operating a medical procedure object accounting system to account for, track or monitor medical procedure instruments and supplies, according to one illustrated embodiment, employing various of the apparatus or devices described in reference to FIGS. 1-10, and particularly suited for use with the structures of FIGS. 8A, 8B and 8C, which employs RFID interrogators or readers associated with a trocar or other medical or clinical procedure instrument.
Figure 11B:
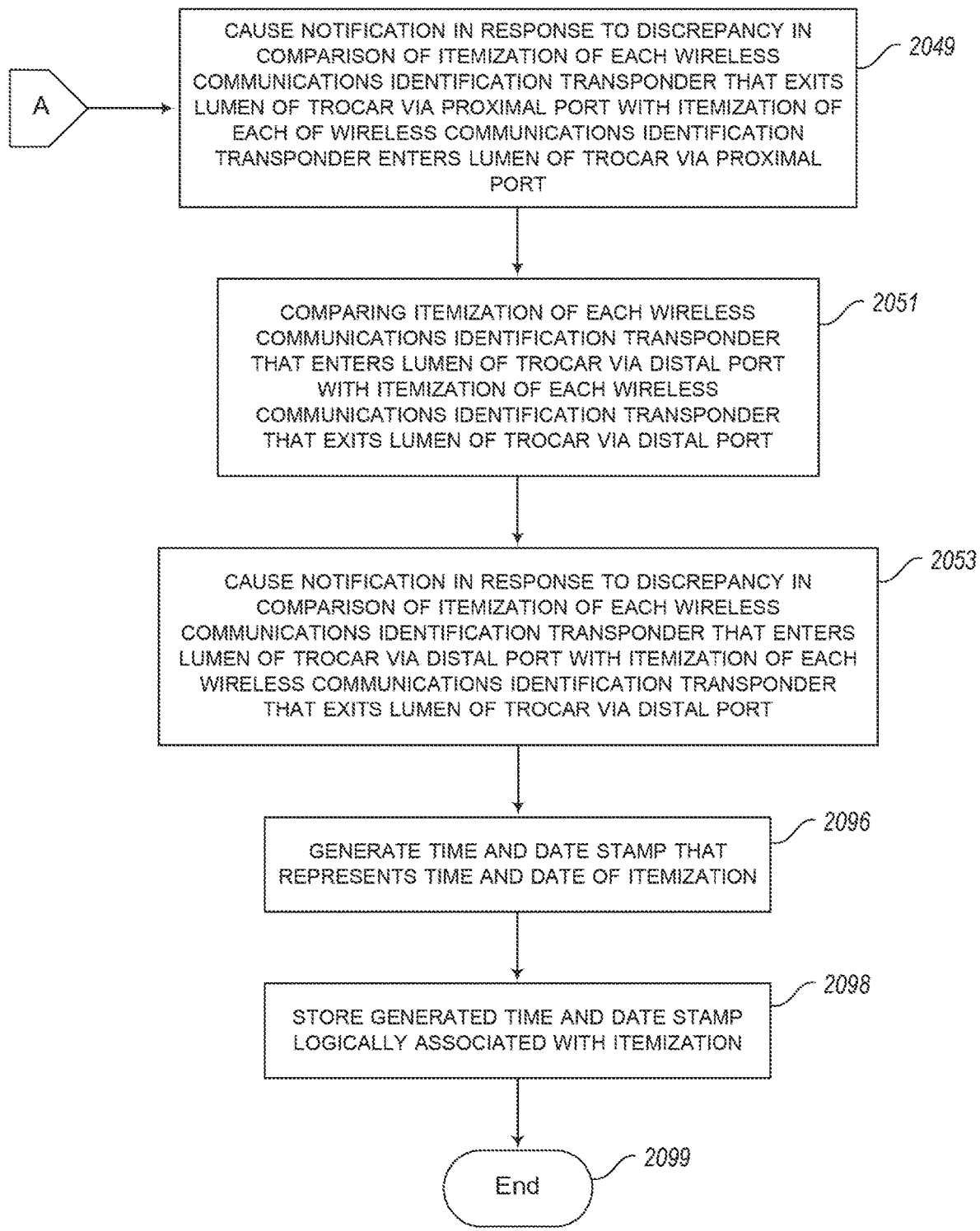

FIGS. 11A-11B show a method 2000 of operating a medical procedure object accounting system to account for, track or monitor medical procedure instruments and supplies, according to one illustrated embodiment. The method 2000 can, for example, be implemented by the structures of FIGS. 8A, 8B and 8C, which employs RFID interrogators or readers associated with a trocar or other medical or clinical procedure instrument.

The method 2000 can be used as a standalone method, or can be employed along with, or even part of, the various other methods described herein.

The method 2000 starts at 2002, for example on power ON of one or more components (e.g., accounting system, RFID interrogators or readers, presence/absence interrogators or readers), on invocation of some calling program, routine, subprogram or function, or for example in response to detection of motion via a suitable motion sensor (e.g., one- or multi-axis accelerometer). Alternatively, the method may start in response to detection of an item (e.g., instrument or supply) entering the trocar, for instance via an entrance or proximal port of a lumen.

At 2012, at least during a first period, one or more trocar RFID antenna(s) of an RFID interrogation system emit RFID interrogation signal(s) having a range that covers at least a portion of an interior of a lumen of a trocar or cannula. The RFID interrogation signals are typically in a first frequency range (e.g., UHF), which is typically a relatively higher frequency than a frequency of interrogation signals for dumb wireless transponders. Such can occur automatically, via autonomous control by an RFID interrogator, or alternatively via manual operation (e.g., activation of a switch or trigger) of an RFID interrogator by the personnel. Typically, the RFID interrogation system will emit RFID interrogation signal(s) via a number of associated trocar RFID antennas, for example positioned and/or oriented at or proximate an entrance or proximal end of the lumen and/or positioned and/or oriented at or proximate an exit or distal end of the lumen to provide limited coverage of a portion of the interior of the lumen of the trocar. In at least some implementations, interrogation can occur as instruments or supplies pass through a portion (e.g., annular portion) of the lumen, for instance an entrance or proximal port and/or an exit or distal port. In at least some implementations, such can occur by passing the instruments and supplies by a respective trocar RFID antenna of the RFID interrogation system, for example one by one. The first period may, for example, be at or proximate a start of the medical or clinical procedure.

At 2014, during the first period, one or more RFID interrogators or readers detect RFID response signal(s) returned from wireless identification transponder(s) in or passing through the lumen of the trocar.

At 2016, one or more RFID interrogators or readers identify wireless identification transponder(s) in or passing through the lumen of the trocar based on RFID response signals detected during the first period.

At 2018, the RFID interrogators or readers or an accounting system adds item entries for each instrument and/or supply (e.g., automatic count in) to an inventory based on the various RFID response signal(s) detected during the first period, for instance in response to receipt of information from one or more RFID interrogators or readers. For example, the accounting system may update a field of a record associated with or corresponding to the particular instrument, supply or RFID transponder physically associated therewith. The inventory can be maintained locally or remotely.

The accounting system can, for example, itemize each of the wireless communications identification transponders and/or associated items that enter the lumen of the trocar via a proximal port (e.g., entrance, proximate the user). The accounting system can, for example, itemize each of the wireless communications identification transponders and/or associated items that exit the lumen of the trocar via the proximate port. The accounting system can, for example, itemize each of the wireless communications identification transponders and/or associated items that enter the lumen of the trocar via a distal port (e.g., exit, distal to the user). The accounting system can, for example, itemize each of the wireless communications identification transponders and/or associated items that exit the lumen of the trocar via the distal port (e.g., exit, proximate patient and obturator).

At 2040, the RFID interrogation system or the accounting system can determine a first count of total number of items that enter lumen of cannula based on detected response signals.

At 2042, the RFID interrogation system or the accounting system can determine a second count of total number of items that exit lumen of cannula based on detected response signals.

At 2047, the RFID interrogation system or the accounting system can compare itemization of each of the wireless communications identification transponders that exits the lumen of the trocar via the proximal port with the itemization of each of the wireless communications identification transponders that enters the lumen of the trocar via the proximal port.

At 2049, the RFID interrogation system or the accounting system can cause a notification to be provided in response to a discrepancy in the comparison of the itemization of each of the wireless communications identification transponders that exits the lumen of the trocar via the proximal port with the itemization of each of the wireless communications identification transponders that enters the lumen of the trocar via the proximal port. The notification can, for example, take the form of a visual and/or aural alert. Such can be provided via a display monitor, speakers and/or a heads up or head-worn device, e.g., a virtual reality or augmented reality head set.

At 2051, the RFID interrogation system or the accounting system can compare the itemization of each of the wireless communications identification transponders that enters the lumen of the trocar via the distal port with the itemization of each of the wireless communications identification transponders that exits the lumen of the trocar via the distal port.

At 2053, the RFID interrogation system or the accounting system can cause notification to be provided in response to a discrepancy in the comparison of the itemization of each of the wireless communications identification transponders that enters the lumen of the trocar via the distal port with the itemization of each of the wireless communications identification transponders that exits the lumen of the trocar via the distal port. The notification can, for example, take the form of a visual and/or aural alert. Such can be provided via a display monitor, speakers and/or a heads up or head-worn device, e.g., a virtual reality or augmented reality head set.

Optionally at 2096, the accounting system can generate a time and date stamp that represents a time and date of the itemization.

Optionally at 2098, the accounting system or some other component stores the time and date stamp associated with inventory in tamper-proof form. For example, the accounting system can generate a hash based on the accounting and inventory and time and date stamp and store the same, allowing such to be later validated by authorized parties.

The method 2000 terminates at 2099, for example until invoked again. In some implementations, the method 2000 may be executed repeatedly, even continuously, or periodically or aperiodically. The method 2000 can be implemented as multiple threads, for example via a multi-threaded processor.

Figure 12:
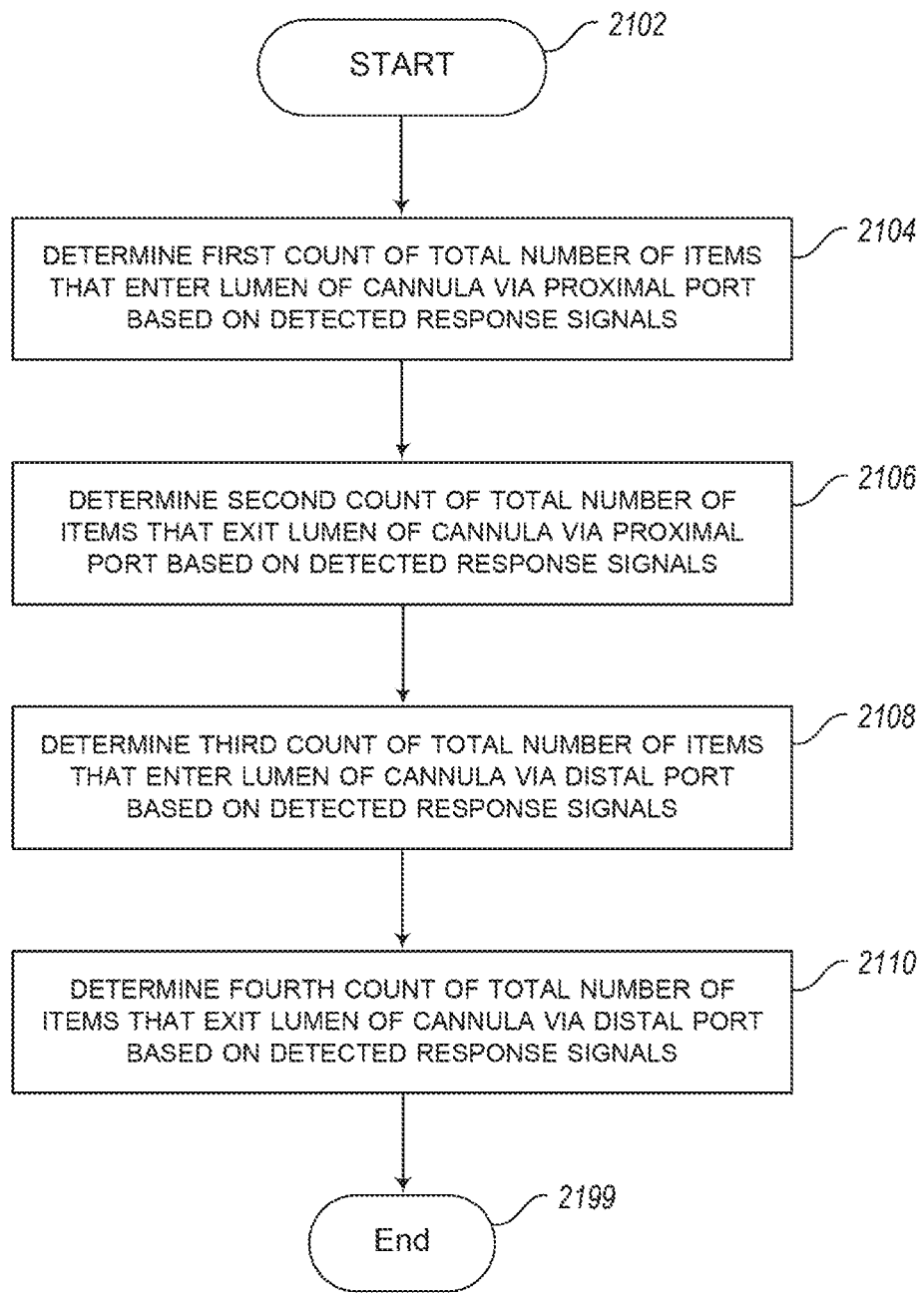
FIG. 12 is a flow diagram showing a workflow or method of operation in a medical or clinical environment according to at least one implementation, for example as part of the workflow or method of FIGS. 11A-11B.

FIG. 12 is a flow diagram showing a workflow or method of operation in a medical or clinical environment according to at least one implementation, for example as part of the workflow or method 2000 of FIGS. 11A-11B.

The method 2100 starts at 2102. At 2104, an RFID interrogation system or an accounting system determines a first count of a total number of items that enter the lumen of the cannula via a proximal port (e.g., entrance, proximate the user) based on the detected response signals. For example, the range of a first antenna positioned at or proximate the proximal port can be limited to cover an interior volume of the lumen at or proximate the proximal port without also covering an interior volume of the lumen at or proximate a proximal port. In some implementations, two spaced apart antennas (e.g., 1002a and 1002c; 1002b and 1002d; 1002a and 1002b) may be employed to detect a relative direction of travel of an item and associated RFID transponder in the trocar. The RFID interrogation system or an accounting system can, for example, determine direction (e.g., ingress or egress via the proximal port) of the item and associated RFID transponder based on a timing or sequence of detection of the given RFID transponder by each of the two antennas. Thus, if a given RFID transponder is detected by a first antenna relatively upstream (i.e., direction of flow is from the entrance or proximal port toward the exit or distal port) before detection by a relatively downstream one of the antennas, the item and associated RFID are passing in a first direction (e.g., advancing) along the lumen of the trocar. Conversely, if a given RFID transponder is detected by a relatively downstream one of the antennas before detection by a relatively upstream one of the antennas, the item and associated RFID are passing in a second direction (e.g., being withdrawn). In some implementations, two antennas can be located at or proximate respective ends of the trocar or lumen. In some implementations, two closely spaced antennas may be positioned at or proximate the proximal port, each of these antennas spaced relatively from one another. Additionally or alternatively, in some implementations, two closely spaced antennas may be positioned at or proximate the distal port, each of these antennas spaced relatively from one another.

At 2106, the RFID interrogation system or the accounting system determines a second count of a total number of items that exit the lumen of the cannula via the proximal port based on the detected response signals.

At 2108, the RFID interrogation system or the accounting system determine a third count of a total number of items that enter the lumen of the cannula via a distal port (e.g., exit, proximate patient and obturator) based on the detected response signals. For example, the range of a second antenna positioned at or proximate the distal port can be limited to cover an interior volume of the lumen at or proximate the distal port without also covering an interior volume of the lumen at or proximate the proximal port.

At 2110, the RFID interrogation system or the accounting system determine a fourth count of a total number of items that exit the lumen of the cannula via the distal port based on the detected response signals.

The method 2100 terminates at 2199, for example until invoked again. In some implementations, the method 2100 may be executed repeatedly, even continuously, or periodically or aperiodically. The method 2100 can be implemented as multiple threads, for example via a multi-threaded processor.

Transponders useful for marking medical procedure related objects may take a variety of forms. Transponders capable of withstanding sterilization procedures would be particularly advantageous. A permanent memory type RFID transponder which retains information or data, for instance a unique identifier, and which is substantially gamma ray resistant and capable of being subjected to the relatively high temperatures often associated with sterilization may be formed from an antenna, passive power or backscatter circuit and a permanent memory circuit communicatively coupled to the antenna and powered via the passive power or backscatter circuit to transmit the contents of the permanent memory in response to power derived from an interrogation signal. The permanent memory circuit may advantageously take the form or may incorporate aspects of the permanent memory circuits described in one or more of U.S. Pat. Nos. 7,609,538; 7,471,541; 7,269,047; 7,042,722; 7,031,209; 6,992,925; 6,972,986; 6,956,258; 6,940,751; 6,898,116; 6,856,540; 6,822,888; 6,798,693; 6,791,891; 6,777,757; 6,766,960; 6,700,151; 6,671,040; 6,667,902; and 6,650,143, all of which are incorporated herein by reference in their entireties to the extent that such are not inconsistent with the other portions of present detailed description. Applicants have recognized that such permanent memory circuits may be resistant to gamma ray radiation, chemicals (e.g., peroxide) and/or high temperatures, and thus may be particularly suitable for use in manufacturing transponders for use in marking objects that will be subjected to the extremes of sterilization. The permanent memory type transponder may include a housing, shell or encapsulant. Such a permanent memory transponder may be particularly useful for marking gauze or sponges. Such a transponder may be attached to a medical procedure related object in any variety of fashions, including sewn to, sewn in, adhered via adhesives or heat or RF welding, riveted, tied to, via a snap, stapled, etc.

Various structures are referred to as shielded, that is shielded at least from certain radio frequencies or wavelengths and/or microwave frequencies or wavelength in the frequency ranges or wavelength ranges at which the wireless transponders and associated interrogators operate, i.e., frequency ranges or wavelength ranges of interrogation signals transmitted by the interrogators and/or frequency ranges or wavelength ranges of response signals returned by wireless transponders. The shield may be a Faraday cage, that sufficiently attenuates electromagnetic signals as to prevent communication between the interrogator(s) and the wireless transponder(s). The shield (e.g., Faraday cage) can comprise sheets and/or meshes of conductive material (e.g., aluminum, copper, silver, gold, mild steel), of sufficient conductivity, thickness, and geometry as to cause attenuation (e.g., 50 dB; 60 dB reduction via a silver coated nylon fabric; 85 dB reduction via aluminum foil, 120 dB reduction via Mu-copper foil of 0.12 mm thick) in the particular wavelength or frequency ranges of interest (e.g., 125 kHz, 13.5 MHz, 900 MHz, and 3.5-5.8 MHz). Where a mesh is employed, the holes or apertures of the mesh should have a characteristic dimension that is much smaller (e.g., ¼ wavelength) than the wavelength of the signal to be stopped (i.e., interrogation signal and/or response signal).

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

Also for instance, many of the embodiments described herein, perform interrogation and detection of transponder tagged objects using multiple antennas. Successive ones of the antennas may be used to transmit an interrogation signal, while two or more antennas are monitored for a response to the interrogation signal. Such may provide significant advantages over more conventional methods, for example motion-based methods that employ motion (e.g., sweeping) of an antenna (e.g., wand) over a patient. For instance, this allows the transmit and receive paths to the transponder to be different from one another (e.g., the transmit path is from a first antenna to a transponder, while the receive path is from the transponder to a second antenna). Hence, the path length to the transponder may be shortened in many configurations, thus improving the signal. For instance, when using a single antenna to both transmit an interrogation signal and to receive a response to the interrogation signal, the power of the received signal is equal to about the 6th root of the input power. However, when using multiple antennas to transmit and receive over the same area, interrogation path length in one direction may be shorter. Another advantage is that all scan time may be averaged, allowing a longer noise time averaging (e.g., 10 seconds) as opposed to motion-based scanning, where integration time may be limited (e.g., about 0.25 seconds per sample). Even further, a representative value of noise samples measured over a plurality of antennas may be employed to determine noise to be removed from noise plus signals received at one of the antennas, thereby advantageously lowering a noise floor and/or increasing range or performance. Thus, the various disclosed embodiments may provide significantly better performance.

While generally discussed in terms of trocars, the various teachings herein can be applied to other instruments, for example other medical instruments with channels or with tubular bodies (e.g., cylindrical, rectangular, and/or hexagonal tube), for instance syringes.

While generally discussed in terms of a passive wireless transponder, which requires an interrogation signal to derive electrical energy to power operation, for example to backscatter a response signal, such is not necessary to all implementations. For example, some implementations can employ an active transponder, with an onboard, consumable power source (e.g., chemical battery), which can emit signals from time-to-time (e.g., periodically) without any external stimulus (e.g., interrogation signals). Such implementations are of course subject to the power source being capable of operating over long times, even if the object to which the active wireless transponder is attached is not put into service for several years. Thus, most implementations will employ passive wireless transponders, and thus employ interrogation signals.

In some embodiments, a high speed LINUX-based microprocessor may be employed in the console. In some embodiments, an LCD touch screen may be employed as a user interface device. Some embodiments may include update-ready software images for new applications. Such may facilitate the automatic loading of instructions on detection of a new device. RF reading may be performed using a handheld wand, via antennas located at the various nursing stations, a standalone handheld RFID reader, and/or via antennas positioned to interrogate all or part of a body. A PDR log may be maintained. Information may be offloaded in a variety of fashions, for instance a memory stick, wireless data transfer, or printer. An optional monitor may be coupled to the presence/absence interrogator or reader to display video or other images. In some embodiment, one or more machine-readable symbol readers may be coupled to the presence/absence interrogator or reader to read machine-readable symbols and transfer read data to the console. In some embodiments, a reading or scanning device (e.g., handheld antenna, handheld RFID reader, machine-readable symbol readers, antenna position to reader items on various tables and stands or nursing stations) may be a USB device, which automatically uploads counting or accounting instructions (e.g., software) to a presence/absence interrogator or reader when communicatively coupled thereto. The reading or scanning device may be appropriate for use with aseptic techniques, for example via placement under a drape or otherwise covered, or having been sterilized (e.g., autoclave). The reader or scanning device may be an antenna suitable for interrogating RFID transponders or a reader suitable for interrogating RFID transponders. Such may be incorporated in a mat, dish, tray or packed coil apparatus. Such may be used as a check in and/check out apparatus to ensure management or accounting of objects in the medical procedure environment. A suitable antenna may be a coil that enables object reading in random orientations over specific portions of nurse management areas (e.g., instrument or supply tables or stands).

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various exemplary methods or processes are described. It is noted that these exemplary methods or processes may include additional acts and/or may omit some acts. In some implementations, the acts of the various exemplary methods or processes may be performed in a different order and/or some acts may be executed or performed concurrently.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Pat. No. 6,026,818, issued Feb. 22, 2000; U.S. Patent Publication No. US2004/0250819, published Dec. 16, 2004; U.S. Pat. No. 8,710,957, issued Apr. 29, 2014; U.S. Pat. No. 7,898,420, issued Mar. 1, 2011; U.S. Pat. No. 7,696,877, issued Apr. 13, 2010; U.S. Pat. 8,358,212, issued Jan. 22, 2013; U.S. Pat. No. 8,111,162, issued Feb. 7, 2012; U.S. Pat. No. 8,354,931, issued Jan. 15, 2013; U.S. Patent Publication No. US2010/0108079, published May 6, 2010; U.S. Patent Publication No. US2010/0109848, published May 6, 2010; U.S. Patent Publication No. US2011/0004276, published Jan. 6, 2011; U.S. Patent Publication No. US2011/0181394, published Jul. 28, 2011; U.S. Patent Publication No. US2013/0016021, published Jan. 17, 2013; PCT Patent Publication No. WO 2015/152975, published Oct. 8, 2015; U.S. Provisional patent application Ser. No. 62/143,726 filed Apr. 6, 2015; U.S. Provisional patent application Ser. No. 62/182,294 filed Jun. 19, 2015; U.S. Provisional patent application Ser. No. 62/164,412 filed May 20, 2015; U.S. Non-Provisional patent application Ser. No. 14/523,089 filed Oct. 24, 2014; U.S. Non-Provisional patent application Ser. No. 14/327,208 filed Jul. 9, 2014; U.S. Non-Provisional patent application Ser. No. 15/003,515 filed Jan. 21, 2016; U.S. Non-Provisional patent application Ser. No. 15/003,524 filed Jan. 21, 2016; U.S. Non-Provisional patent application Ser. No. 15/052,125 filed Feb. 24, 2016; U.S. Non-Provisional patent application Ser. No. 15/053,965 filed Feb. 25, 2016; U.S. Provisional patent application Ser. No. 62/360,864 filed Jul. 11, 2016 and entitled "METHOD AND APPARATUS TO ACCOUNT FOR TRANSPONDER TAGGED OBJECTS USED DURING CLINICAL PROCEDURES, EMPLOYING A SHIELDED RECEPTACLE"; U.S. Provisional patent application Ser. No. 62/360,866 filed Jul. 11, 2016 and entitled "METHOD AND APPARATUS TO ACCOUNT FOR TRANSPONDER TAGGED OBJECTS USED DURING CLINICAL PROCEDURES EMPLOYING A SHIELDED RECEPTACLE WITH ANTENNA"; and U.S. Provisional patent application Ser. No. 62/360,868 filed Jul. 11, 2016 and entitled "METHOD AND APPARATUS TO ACCOUNT FOR TRANSPONDER TAGGED OBJECTS USED DURING CLINICAL PROCEDURES, FOR EXAMPLE INCLUDING COUNT IN AND/OR COUNT OUT AND PRESENCE DETECTION", are each incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula;
   at least one trocar antenna, the at least one trocar antenna physically coupled to the trocar and positioned and oriented to provide wireless communications coverage of at least a portion of the interior of the lumen and any wireless communications transponders that pass through the lumen of the cannula; and
   an interrogator communicatively coupled to the at least one trocar antenna and operable to cause the at least one trocar antenna to emit at least one of radio or microwave frequency energy interrogation signals and to detect response signals from any exposed wireless communications transponders that pass through the lumen of the cannula,
   wherein the at least one trocar antenna is communicatively detachably coupled to the interrogator via at least one electrical cable and a plug.

2. The apparatus of claim 1 wherein the at least one trocar antenna is communicatively coupled to the interrogator via at least one electrical cable.

3. The apparatus of claim 1 wherein the at least one trocar antenna is positioned and oriented to provide coverage of the proximal port and all wireless communications transponders passing through the proximal port.

4. The apparatus of claim 1 wherein the trocar further includes a seal located at least proximate the proximal end and an obturator that movingly extends through the cannula with a piercing tip located proximate the distal end.

5. The apparatus of claim 1 wherein the proximal port is sized and dimensioned to receive pieces of disposable gauze, each piece of disposable gauze tagged with a respective dumb wireless communications transponder that does not store any unique identifier nor provide any unique identifier.

6. The apparatus of claim 1 wherein the proximal port is sized and dimensioned to receive pieces of disposable gauze, each piece of disposable gauze tagged with a respective radio frequency identification (RFID) wireless communications identification transponder.

7. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; and
   at least one trocar antenna, the at least one trocar antenna physically coupled to the trocar and positioned and oriented to provide wireless communications coverage of at least a portion of the interior of the lumen and any wireless communications transponders that pass through the lumen of the cannula,
   wherein the cannula of the trocar shields the at least one trocar antenna from response signals emitted by any wireless communications transponders in the exterior of the cannula.

8. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; and
   at least one trocar antenna, the at least one trocar antenna physically coupled to the trocar and positioned and oriented to provide wireless communications coverage of at least a portion of the interior of the lumen and any wireless communications transponders that pass through the lumen of the cannula, wherein the at least one trocar antenna comprises at least one electrically conductive coil that is concentric with at least one of the proximal port, the distal port or the lumen.

9. The apparatus of claim 8 wherein the cannula of the trocar comprises a metal.

10. The apparatus of claim 9 wherein the at least one trocar antenna includes an electrically insulative sheath that electrically insulates the at least one trocar antenna from the cannula.

11. The apparatus of claim 8 wherein the cannula of the trocar comprises a plastic.

12. The apparatus of claim 11 wherein the at least one trocar antenna is encased in the plastic of the cannula.

13. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; and
   at least one trocar antenna, the at least one trocar antenna physically coupled to the trocar and positioned and oriented to provide wireless communications coverage of at least a portion of the interior of the lumen and any wireless communications transponders that pass through the lumen of the cannula, wherein the at least one trocar antenna is positioned and oriented to provide coverage of an entirety of the interior of the lumen of the cannula and all wireless communications transponders in the interior of the lumen of the cannula.

14. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; and
   at least one trocar antenna, the at least one trocar antenna physically coupled to the trocar and positioned and oriented to provide wireless communications coverage of at least a portion of the interior of the lumen and any wireless communications transponders that pass through the lumen of the cannula, wherein the at least one trocar antenna is positioned and oriented to provide coverage of the distal port and all wireless communications transponders passing through the distal port.

15. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; and
   at least one trocar antenna, the at least one trocar antenna physically coupled to the trocar and positioned and oriented to provide wireless communications coverage of at least a portion of the interior of the lumen and any wireless communications transponders that pass through the lumen of the cannula, wherein the at least one trocar antenna includes a first trocar antenna positioned and oriented to provide coverage of the proximal port and all wireless communications transponders passing through the proximal port, and at least a second trocar antenna positioned and oriented to provide coverage of the distal port and all wireless communications transponders passing through the distal port.

16. An apparatus for use in clinical environments, the apparatus comprising:
   a trocar, the trocar having a cannula with a proximal end and a distal end, the cannula delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula;
   at least one trocar antenna, the at least one trocar antenna physically coupled to the trocar and positioned and oriented to provide wireless communications coverage of at least a portion of the interior of the lumen and any wireless communications transponders that pass through the lumen of the cannula; and
   an interrogator communicatively coupled to the at least one trocar antenna and operable to cause the at least one trocar antenna to emit at least one of radio or microwave frequency energy interrogation signals and to detect response signals from any exposed wireless communications transponders that pass through the lumen of the cannula, wherein the interrogator comprises at least one radio frequency identification (RFID) interrogator communicatively coupled to the at least one trocar antenna and operable to cause the at least one trocar antenna to emit at least one of radio or microwave frequency energy interrogation signals and to detect response signals from any wireless communications identification transponders in the interior of the lumen without detecting any wireless communications identification transponders that are outside the interior of the lumen, wherein the at least one RFID interrogator comprises:
      at least one processor, the at least one processor communicatively coupled to the at least one RFID interrogator; and
      at least one nontransitory processor-readable medium that stores at least one of processor-executable instructions or data, execution of which causes the at least one processor to:
         itemize each of the wireless communications identification transponders that exits the lumen of the trocar via the distal port; and
         itemize each of the wireless communications identification transponders that enters the lumen of the trocar via the distal port.

17. The apparatus of claim 16 wherein the at least one RFID interrogator comprises:
   at least one processor, the at least one processor communicatively coupled to the at least one RFID interrogator; and
   at least one nontransitory processor-readable medium that stores at least one of processor-executable instructions or data, execution of which causes the at least one processor to:
      store an itemization of each of the wireless communications identification transponders that pass through at least a portion of the interior of the lumen.

18. The apparatus of claim 16 wherein the at least one RFID interrogator comprises:
   at least one processor, the at least one processor communicatively coupled to the at least one RFID interrogator; and at least one nontransitory processor-readable medium that stores at least one of processor-executable instructions or data, execution of which causes the at least one processor to:
- itemize each of the wireless communications identification transponders that enters the lumen of the trocar via the proximal port; and
- itemize each of the wireless communications identification transponders that exits the lumen of the trocar via the proximal port.

19. The apparatus of claim 18 wherein execution of the at least one of processor-executable instructions or data further cause the at least one processor to:
compare the itemization of each of the wireless communications identification transponders that exits the lumen of the trocar via the proximal port with the itemization of each of the wireless communications identification transponders that enters the lumen of the trocar via the proximal port.

20. The apparatus of claim 16 wherein execution of the at least one of processor-executable instructions or data further cause the at least one processor to:
compare the itemization of each of the wireless communications identification transponders that enters the lumen of the trocar via the distal port with the itemization of each of the wireless communications identification transponders that exits the lumen of the trocar via the distal port.

* * * * *